United States Patent
Dole et al.

(10) Patent No.: US 11,447,802 B2
(45) Date of Patent: Sep. 20, 2022

(54) MICROORGANISMS AND PROCESSES FOR LACTIC ACID PRODUCTION

(71) Applicant: PTT Global Chemical Public Company Limited, Bangkok (TH)

(72) Inventors: Sudhanshu Vijay Dole, Andover, MA (US); Theron Hermann, Arlington, MA (US); Sean Joseph Regan, Worcester, MA (US); Mark Andrew Sheff, Westwood, MA (US); Russell Lizardo Udani, Arlington, MA (US); R. Rogers Yocum, Lexington, MA (US)

(73) Assignee: PTT Global Chemical Public Company Limited, Bangkok (TH)

( * ) Notice: Subject to any disclaimer, the term of this patent is extended or adjusted under 35 U.S.C. 154(b) by 0 days.

(21) Appl. No.: 16/969,712

(22) PCT Filed: Feb. 15, 2019

(86) PCT No.: PCT/IB2019/000178
§ 371 (c)(1),
(2) Date: Aug. 13, 2020

(87) PCT Pub. No.: WO2019/159011
PCT Pub. Date: Aug. 22, 2019

(65) Prior Publication Data
US 2021/0017551 A1 Jan. 21, 2021

Related U.S. Application Data

(60) Provisional application No. 62/631,541, filed on Feb. 16, 2018.

(51) Int. Cl.
*C12P 7/56* (2006.01)
*C12N 1/18* (2006.01)
*C12R 1/85* (2006.01)

(52) U.S. Cl.
CPC ............. *C12P 7/56* (2013.01); *C12N 1/185* (2021.05); *C12R 2001/85* (2021.05); *C12Y 101/01027* (2013.01); *C12Y 106/99003* (2013.01); *C12Y 301/03021* (2013.01); *C12Y 401/01001* (2013.01); *C12Y 401/01032* (2013.01)

(58) Field of Classification Search
CPC .... C12Y 401/01032; C12Y 106/99003; C12Y 401/01001; C12Y 301/03021; C12Y 101/01027; C12N 1/185; C12N 1/205; C12N 9/0006; C12P 7/56; C12R 2001/85; C12R 2001/01
See application file for complete search history.

(56) References Cited

U.S. PATENT DOCUMENTS

| | | | | |
|---|---|---|---|---|
| 7,049,108 B2* | 5/2006 | Porro | ................... | C07K 14/395 435/135 |
| 7,229,805 B2* | 6/2007 | Rajgarhia | ................. | C12P 7/40 435/139 |
| 8,137,953 B2* | 3/2012 | Miller | .................. | C12N 9/0006 435/254.2 |
| 11,072,807 B2* | 7/2021 | Yocum | ................. | C12N 9/0008 |
| 2015/0315616 A1 | 11/2015 | Dundon et al. | | |

FOREIGN PATENT DOCUMENTS

WO    WO 2019/159011 A3    8/2019

OTHER PUBLICATIONS

Chica et al., Semi-rational approaches to engineering enzyme activity: combining the benefits of directed evolution and rational design. Curr. Opi. Biotechnol., 2005, vol. 16: 378-384. (Year: 2005).*
Das et al., Enantioselective Oxidation of 2-Hydroxy Carboxylic Acids by Glycolate Oxidase and Catalase Coexpressed in Methylotrophic Pichia pastoris Biotechnol. Prog., 2010, vol. 26(3): 607-615. (Year: 2010).*
Kisselev L., Polypeptide release factors in prokaryotes and eukaryotes: same function, different structure. Structure, 2002, vol. 10: 8-9. (Year: 2002).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Bae et al., Direct fermentation of Jerusalem artichoke tuber powder for production of L-lactic acid and D-lactic acid by metabolically engineered Kluyveromyces marxianus. J. Biotechnol., 2018, vol. 266: 27-33. (Year: 2018).*
Lee et al., Co-expression of two heterologous lactate dehydrogenases genes in Kluyveromyces marxianus for L-lactic acid production. J. Biotechnol., 2017, vol. 241: 81-86. (Year: 2017).*
Chemspider; 3-chlorolactate structure, 2 pages downloaded from Royal Society of Chemistry, Feb. 9, 2022 (Year: 2022).*
International Search Report and Written Opinion dated Aug. 28, 2019 in PCT/IB19/00178, 13 pages.

(Continued)

*Primary Examiner* — Ganapathirama Raghu
(74) *Attorney, Agent, or Firm* — Oblon, McClelland, Maier & Neustadt, L.L.P.

(57) ABSTRACT

Yeast strains and fermentation process for producing D-lactic acid and L-lactic acid are disclosed with higher titer, higher yield, shorter time, lower pH, and higher average specific productivity.

10 Claims, 8 Drawing Sheets

Specification includes a Sequence Listing.

(56) References Cited

OTHER PUBLICATIONS

Ilmén, M., et al., "Production of L-lactic acid by the yeast *Candida sonorensis* expressing heterologous bacterial and fungal lactate dehydrogenases", Microbial Cell Factories, vol. 12, No. 53, 2013, pp. 1-15.
Lee, J.Y., et al., "Engineering Cellular Redox Balance in *Saccharomyces cerevisiae* for Improved Production of L-Lactic Acid", Biotechnology and Bioengineering, vol. 112, No. 4, Apr. 2015, pp. 751-758.
Sherman, F., et al., "Mutants of Yeast Defective in ISO-1-CYTOCHROME", Genetics, vol. 77, Jun. 1974, pp. 255-284.
Yamada, R., et al., "Enhanced D-lactic Acid Production by Recombinant *Saccharomyces cerevisiae* Following Optimization of the Global Metabolic Pathway", Biotechnology and Bioengineering, vol. 114, No. 9, Sep. 2017, pp. 2075-2084.
Casal, M., et al., "Lack of lactate-proton symport activity in pck1 mutants of *Saccharomyces cerevisiae*", FEMS Microbiology Letters, vol. 128, 1995, pp. 279-282.
Orlandi, I., et al., "Ethanol and Acetate Acting as Carbon/Energy Sources Negatively Affects Yeast Chronological Aging", Hindawi Publishing Corporation, Oxidative Medicine and Cellular Longevity, vol. 2013, article ID 802870 pp. 1-10 with cover page.

\* cited by examiner wt URA3 PCR product
2883 bp

SEQUENCE LISTING

<160> NUMBER OF SEQ ID NOS: 6

<210> SEQ ID NO 1
<211> LENGTH: 10203
<212> TYPE: DNA
<213> ORGANISM: Kluyveromyces marxianus

<400> SEQUENCE: 1

```
gtggcggttt tcatggcttg ttatgactgt ttttttgggg tacagtctat gcctcgggca    60
tccaagcagc aagcgcgtta cgccgtgggt cgatgtttga tgttatggag cagcaacgat   120
gttacgcagc agggcagtcg ccctaaaaca aagttaaaca tcatgaggga agcggtgatc   180
gccgaagtat cgactcaact atcagaggta gttggcgtca tcgagcgcca tctcgaaccg   240
acgttgctgg ccgtacattt gtacggctcc gcagtggatg gcggcctgaa gccacacagt   300
gatattgatt tgctggttac ggtgaccgta aggcttgatg aaacaacgcg gcgagctttg   360
atcaacgacc ttttggaaac ttcggcttcc cctggagaga gcgagattct ccgcgctgta   420
gaagtcacca ttgttgtgca cgacgacatc attccgtggc gttatccagc taagcgcgaa   480
ctgcaatttg gagaatggca gcgcaatgac attcttgcag gtatcttcga gccagccacg   540
atcgacattg atctggctat cttgctgaca aaagcaagag aacatagcgt tgccttggta   600
ggtccagcgg cggaggaact ctttgatccg gttcctgaac aggatctatt tgaggcgcta   660
```

```
aatgaaacct taacgctatg gaactcgccg cccgactggg ctggcgatga gcgaaatgta    720
gtgcttacgt tgtcccgcat ttggtacagc gcagtaaccg gcaaaatcgc gccgaaggat    780
gtcgctgccg actgggcaat ggagcgcctg ccggcccagt atcagcccgt catacttgaa    840
gctagacagg cttatcttgg acaagaagaa gatcgcttgg cctcgcgcgc agatcagttg    900
gaagaatttg tccactacgt gaaaggcgag atcaccaagg tagtcggcaa ataatgtcta    960
acaattcgtt caagccgacg ccgcttcgcg gcgcggctta actcaagcgt tagatgcact   1020
aagcacataa ttgctcacag ccaaactatc agaattctga accagtccta aaacgagtaa   1080
ataggaccgg caattcttca agcaataaac aggaatacca attattaaaa gataacttag   1140
tcagatcgta caataaagct ttgaagaaaa atgcgcctta ttcaatcttt gctataaaaa   1200
atggcccaaa atctcacatt ggaagacatt tgatgacctc atttctttca atgaagggcc   1260
taacggagtt gactaatgtt gtgggaaatt ggagcgataa gcgtgcttct gccgtggcca   1320
ggacaacgta tactcatcag ataacagcaa tacctgatca ctacttcgca ctagtttctc   1380
ggtactatgc atatgatcca atatcaaagg aaatgatagc attgaaggat gagactaatc   1440
caattgagga gtggcagcat atagaacagc taaaggtag tgctgaagga agcatacgat    1500
accccgcatg gaatgggata atatcacagg aggtactaga ctacctttca tcctacataa   1560
atagacgcat ataagtacgc atttaagcat aaacacgcac tatgccgttc ttctcatgta   1620
tatatatata caggcaacac gcagatatag gtgcgacgtg aacagtgagc tgtatgtgcg   1680
cagctcgcgt tgcattttcg gaagcgctcg ttttcggaaa cgctttgaag ttcctattcc   1740
gaagttccta ttctctagaa agtataggaa cttcagagcg ctttgaaaa ccaaaagcgc    1800 tctgaagacg cactttcaaa aaccaaaaa cgcaccggac tgtaacgagc tactaaaata    1860
ttgcgaatac cgcttccaca acattgctc aaaagtatct ctttgctata tatctctgtg    1920
ctatatccct atataaccta cccatccacc tttcgctcct tgaacttgca tctaaactcg   1980
acctctacat tttttatgtt tatctctagt attactcttt agacaaaaaa attgtagtaa   2040
gaactattca tagagtgaat cgaaaacaat acgaaaatgt aaacatttcc tatacgtagt   2100
atatagagac aaaatagaag aaaccgttca taattttctg accaatgaag aatcatcaac   2160
gctatcactt tctgttcaca agtatgcgc aatccacatc ggtatagaat ataatcgggg    2220
atgcctttat cttgaaaaaa tgcacccgca gcttcgctag taatcagtaa acgcgggaag   2280
tggagtcagg cttttttat ggaagagaaa atagacacca aagtagcctt cttctaacct    2340
taacggacct acagtgcaaa aagttatcaa gagactgcat tatagagcgc acaaggaga    2400 aaaaagtaa tctaagatgc tttgttagaa aaatagcgct ctcgggatgc attttttgtag  2460 aacaaaaaag aagtatagat tctttgttgg taaaatagcg ctctcgcgtt gcatttctgt   2520
tctgtaaaaa tgcagctcag attctttgtt tgaaaaatta gcgctctcgc gttgcatttt   2580
tgttttacaa aaatgaagca cagattcttc gttggtaaaa tagcgctttc gcgttgcatt   2640
tctgttctgt aaaaatgcag ctcagattct tgtttgaaa aattagcgct ctcgcgttgc    2700
atttttgttc tacaaaatga agcacagatg cttcgttaac aaagatatgc tattgaagtg   2760
caagatggaa acgcagaaaa tgaaccgggg atgcgacgtg caagattacc tatgcaatag   2820
atgcaatagt ttctccagga accgaaatac atacattgtc ttccgtaaag cgctagacta   2880
tatattatta tacaggttca aatatactat ctgtttcagg gaaactccc aggttcggat    2940 gttcaaaatt caatgatggg taacaagtac gatcgtaaat ctgtaaaaca gtttgtcgga   3000
```

```
tattaggctg tatctcctca aagcgtattc gaatatcatt gagaagctgc agcgtcacat   3060
cggataataa tgatggcagc cattgtagaa gtgccttttg catttctagt ctctttctcg   3120
gtctagctag ttttactaca tcgcgaagat agaatcttag atcacactgc ctttgctgag   3180
ctggatcaat agagtaacaa aagagtggta aggcctcgtt aaaggacaag gacctgagcg   3240
gaagtgtatc gtacagtaga cggagtatac tagtatagtc tatagtccgt ggaattctca   3300
tgtttgacag cttatcatcg attatttcta tccactttaa caccactcct cctagcacag   3360
ctagtaaaac ctcttatagc accatagatg aggctcattt taacgaattt tctctcgaag   3420
cttgaatagc ttagcatagt ggctcttctc atctcatcgc ggaattgaaa aatttcaacc   3480
actataaaat ctattataaa tacagtgaaa agtgccaaga cttctggtga attctaacta   3540
ataaccatac catcatgatt cctgagcaag gtgagcacaa gcttttgtg cagagaaata   3600 ccaacgaaac caaaatccag atcgccattt ccttaaatgg tggtcacatt gaaattccag   3660
agtccatcat aggtaagaag agagttaaaa gtgatggcgt agctacgcaa gctactagtt   3720
ctcaaacgat cgacattcat accggtgtcg gattcctcga ccatatgatt catgctctgg   3780
cgaaacactc tggttggtca ctaatcgttg aatgtattgg tgatttgcac atcgatgatc   3840
accataccac tgaagactgc ggtattgccc taggtgatgc tttcaaacag gccttgggac   3900
aggtacgtgg tgtgaaaaga tttggattcg gttttgcgcc attagatgag ctttatcaa   3960 gagctgttgt cgatctatcc aatagaccat attctgttat tgaattagga ttgaaaagag   4020
aaaaaatcgg tgatttgtcc tgtgaaatga ttccacattt tctagaaagt tttactgaag   4080
cagctagatt gactgttcat gtggactgtt tgagaggttt caacgaccat cacagaagtg   4140
aaagtgcatt taaggcacta gcggtagccc ttagagaagc aacttcacct aatggtacca   4200
acgatgtccc atctacgaag ggtgttctca tgtgaattaa atggcagaaa gtttaaacct   4260
gtatatttat ttacacgata ttatgaaata gtttatttat cgaaattagt caaaatgctt   4320
aacaattctt ctgcatgttt ggtagaatct tcagcacgta ctgcagggtg tctaccacca   4380
gttcttaaag gtctttgttg gtaatttcta ccagacattt gtaatctagc tctgggctt   4440 ataccactaa ccactttagc tcttagcatg actctaccgt tatcctatca gttattaccc   4500
gggaatctcg gtcgtaatga taggtgcctg tcacggctct tttttttactg tacctgtgac   4560 ttcctttctt atttccaagg atgctcatca caatacgctt ctagatctat tatgcattat   4620
aattaatagt tgtagctaca aaaggtaaaa gaaagtccgg ggcaggcaac aatagaaatc   4680
ggcaaaaaaa actacagaaa tactaagagc ttcttcccca ttcagtcatc gcatttcgaa   4740
acaagagggg aatggctctg gctagggaac taaccaccat cgcctgactc tatgcactaa   4800
ccacgtgact acatatatgt gatcgttttt aacattttc aaaggctgtg tgtctggctg   4860
tttccattaa ttttcactga ttaagcagtc atattgaatc tgagctcatc accaacaaga   4920
aatactaccg taaagtgta aaagttcgtt taaatcattt gtaaactgga acagcaagag   4980
gaagtatcat cagctagccc cataaactaa tcaaggagg gagttctccg agaacaagca   5040
gaggttcgag tgtactcgga tcagaagtta caagttgatc gtttatatat aaactataca   5100
gagatgttag agtgtaatgg cattgcgcac attgtatacg ctacaagttt agtcacgtgc   5160
tagaagctgt ttttgcacc gaaaatttt ttttttttt tttttgttt tttggtgaag   5220 gccgggtcac ccggccagcg acatggaggc ccagaatacc ctccttgaca gtcttgacgt   5280
gcgcagctca ggggcatgat gtgactgtcg cccgtacatt tagcccatac atccccatgt   5340
ataatcattt gcatccatac attttgatgg ccgcacggcg cgaagcaaaa attacggctc   5400
```

```
ctcgctgcag acctgcgagc agggaaacgc tcccctcaca gacgcgttga attgtcccca    5460
cgccgcgccc ctgtagagaa atataaaagg ttaggatttg ccactgaggt tcttctttca    5520
tatacttcct tttaaaatct tgctaggata cagttctcac atcacatccg aacataaaca    5580
accatggata gatccggaaa gcctgaactc accgcgacgt ctgtcgagaa gtttctgatc    5640
gaaaagttcg acagcgtctc cgacctgatg cagctctcgg agggcgaaga atctcgtgct    5700
ttcagcttcg atgtaggagg gcgtggatat gtcctgcggg taaatagctg cgccgatggt    5760
ttctacaaag atcgttatgt ttatcggcac tttgcatcgg ccgcgctccc gattccggaa    5820
gtgcttgaca ttggggaatt cagcgagagc ctgacctatt gcatctcccg ccgtgcacag    5880
ggtgtcacgt tgcaagacct gcctgaaacc gaactgcccg ctgttctgca gccggtcgcg    5940
gaggccatgg atgcgatcgc tgcggccgat cttagccaga cgagcgggtt cggcccattc    6000
ggaccgcaag gaatcggtca atacactaca tggcgtgatt tcatatgcgc gattgctgat    6060
ccccatgtgt atcactggca aactgtgatg gacgacaccg tcagtgcgtc cgtcgcgcag    6120
gctctcgatg agctgatgct ttgggccgag gactgccccg aagtccggca cctcgtgcac    6180
gcggatttcg gctccaacaa tgtcctgacg gacaatggcc gcataacagc ggtcattgac    6240
tggagcgagg cgatgttcgg ggattcccaa tacgaggtcg ccaacatctt cttctggagg    6300
ccgtggttgg cttgtatgga gcagcagacg cgctacttcg agcggaggca tccggagctt    6360
gcaggatcgc cgcggctccg ggcgtatatg ctccgcattg gtcttgacca actctatcag    6420
agcttggttg acggcaattt cgatgatgca gcttgggcgc agggtcgatg cgacgcaatc    6480
gtccgatccg gagccgggac tgtcgggcgt acacaaatcg cccgcagaag cgcggccgtc    6540
tggaccgatg gctgtgtaga agtactcgcc gatagtggaa accgacgccc cagcactcgt    6600
ccgagggcaa aggaatagtc agtactgaca ataaaaagat tcttgttttc aagaacttgt    6660
catttgtata gtttttttat attgtagttg ttctatttta atcaaatgtt agcgtgattt    6720 atatttttt tcgcctcgac atcatctgcc cagatgcgaa gttaagtgcg cagaaagtaa    6780
tatcatgcgt caatcgtatg tgaatgctgg tcgctatact gctgtcgatt cgatactaac    6840
gctcaattca tcatttttt tttattcttt ttttgatttt cggtttcttt gaaattttt     6900 tgattcggta atctccgaac agaaggaaga acgaaggaag gagcacagac ttagattggt    6960
atatatacgc atatgtagtg ttgaagaaac atgaaattgc ccagtattct taacccaact    7020
gcacagaaca aaaacctgca ggaaacgaag ataaatcatg tcgaaagcta catataagga    7080
acgtgctgct actcatccta gtcctgttgc tgccaagcta tttaatatca tgcacgaaaa    7140
gcaaacaaac ttgtgtgctt cattggatgt tcgtaccacc aaggaattac tggagttagt    7200
tgaagcatta ggtcccaaaa tttgtttact aaaaacacat gtggatatct tgactgattt    7260
ttccatggag ggcacagtta agccgctaaa ggcattatcc gccaagtaca atttttact    7320 cttcgaagac agaaaatttg ctgacattgg taatacagtc aaattgcagt actctgcggg    7380
tgtatacaga atagcagaat gggcagacat tacgaatgca cacggtgtgg tgggcccagg    7440
tattgttagc ggtttgaagc aggcggcaga agaagtaaca aaggaaccta gaggcctttt    7500
gatgttagca gaattgtcat gcaagggctc cctatctact ggagaatata ctaagggtac    7560
tgttgacatt gcgaagagcg acaaagattt tgttatcggc tttattgctc aaagagacat    7620
gggtggaaga gatgaaggtt acgattggtt gattatgaca cccggtgtgg gtttagatga    7680
caagggagac gcattgggtc aacagtatag aaccgtggat gatgtggtct ctacaggatc    7740
```

```
tgacattatt attgttggaa gaggactatt tgcaaaggga agggatgcta aggtagaggg      7800
tgaacgttac agaaaagcag gctgggaagc atatttgaga agatgcggcc agcaaaacta      7860
aaaaactgta ttataagtaa atgcatgtat actaaactca caaattagag cttcaattta      7920
attatatcag ttattacccg ggaatctcgg tcgtaatgat ttttataatg acgaaaaaaa      7980
aaaaattgga agaaaaagc ttttcagct ttgagaatac cattgtgccg ttgaagcaat        8040
tagcagagaa acacaagttt ttgatatttg aagacaggaa gtttgccgac attgggaaca      8100
ctgttaaatt acaatacacg tctggtgtat accgtatcgc cgaatggtct gatatcacca      8160
atgcacacgg tgtgactggt gcgggcattg ttgctggttt gaagcaaggt gccgaggaag      8220
ttacgaaaga acctagaggg ttgttaatgc ttgccgagtt atcgtccaag gggtctctag      8280
cgcacggtga atacactcgt gggaccgtgg aaattgctaa gagtgataag gactttgtta      8340
ttggatttat tgctcaaaac gatatgggtg aagagaaga gggctacgat tggttgatca      8400
tgacgccagg tgttggtctt gatgacaaag gtgatgcttt gggacaacaa tacagaactg      8460
tggatgaagt tgttgccggt ggatcagaca tcattattgt tgacatgaat ggtcttcggt      8520
ttccgtgttt cgtaaagtct ggaaacgcgg aagtcagcgc cctgcaccat tatgttccgg      8580
atctgcatcg caggatgctg ctggctaccc tgtggaacac ctacatctgt attaacgaag      8640
cgctggcatt gaccctgagt gatttttctc tggtcccgcc gcatccatac cgccagttgt      8700
ttaccctcac aacgttccag taaccgggca tgttcatcat cagtaacccg tatcgtgagc      8760
atcctctctc gtttcatcgg tatcattacc cccatgaaca gaaattcccc cttacacgga      8820
ggcatcaagt gaccaaacag gaaaaaaccg cccttaacat ggcccgcttt atcagaagcc      8880
agacattaac gcttctggag aaactcaacg agctggacgc ggatgaacag gcagacatct      8940
gtgaatcgct tcacgaccac gctgatgagc tttaccgcag ctgcctcgcg cgtttcggtg      9000
atgacggtga aacctctga cacatgcagc tcccggagac ggtcacagct tgtctgtaag       9060
cggatgccgg gagcagacaa gcccgtcagg gcgcgtcagc gggtgttggc gggtgtcggg      9120
gcgcagccat gacccagtca cgtagcgata gcggagtgta tactggctta actatgcggc      9180
atcagagcag attgtactga gagtgcacca tatgcggtgt gaaataccgc acagatgcgt      9240
aaggagaaaa taccgcatca ggcgctcttc cgcttcctcg ctcactgact cgctgcgctc      9300
ggtcgttcgg ctgcggcgag cggtatcagc tcactcaaag gcggtaatac ggttatccac      9360
agaatcaggg gataacgcag gaaagaacat gtgagcaaaa ggccagcaaa aggccaggaa      9420
ccgtaaaaag gccgcgttgc tggcgttttt ccataggctc cgcccccctg acgagcatca      9480
caaaaatcga cgctcaagtc agaggtggcg aaacccgaca ggactataaa gataccaggc      9540
gtttccccct ggaagctccc tcgtgcgctc tcctgttccg accctgccgc ttaccggata      9600
cctgtccgcc tttctccctt cgggaagcgt ggcgctttct catagctcac gctgtaggta      9660
tctcagttcg gtgtaggtcg ttcgctccaa gctgggctgt gtgcacgaac cccccgttca      9720
gcccgaccgc tgcgccttat ccggtaacta tcgtcttgag tccaacccgg taagacacga      9780
cttatcgcca ctggcagcag ccactggtaa caggattagc agagcgaggt atgtaggcgg      9840
tgctacagag ttcttgaagt ggtggcctaa ctacggctac actagaagga cagtatttgg      9900
tatctgcgct ctgctgaagc cagttacctt cggaaaaaga gttggtagct cttgatccgg      9960
caaacaaacc accgctggta gcggtggttt tttgtttgc aagcagcaga ttacgcgcag       10020
aaaaaaagga tctcaagaag atcctttgat cttttctacg ggtctgacg ctcagtgaa        10080 cgaaaactca cgttaaggga ttttggtcat gagattatca aaaaggatct tcacctagat      10140
```

```
cctttaaat taaaaatgaa gttttaaatc aatctaaagt atatatgagt aaacttggtc    10200
tga                                                                10203

<210> SEQ ID NO 2
<211> LENGTH: 7266
<212> TYPE: DNA
<213> ORGANISM: Kluyveromyces marxianus

<400> SEQUENCE: 2
ggcgcgggag attgataaga cttttctagt tgcatatctt ttatatttaa atcttatcta      60
ttagttaatt ttttgtaatt tatccttata tatagtctgg ttattctaaa atatcatttc    120
agtatctaaa aattcccctc tttttcagt tatatcttaa caggcgacag tccaaatgtt     180
gatttatccc agtccgattc atcagggttg tgaagcattt tgtcaatggt cgaaatcaca    240
tcagtaatag tgcctcttac ttgcctcata gaatttcttt ctcttaacgt caccgtttgg    300
tcttttatag tttcgaaatc tatggtgata ccaaatggtg ttcccaattc atcgttacgg    360
gcgtattttt taccaattga agtattggaa tcgtcaattt taaagtatat ctctctttta    420
cgtaaagcct gcgagatcct cttaagtata gcggggaagc catcgttatt cgatattgtc    480
gtaacaaata ctttgatcgg cgctatctgt aatggaaaca tgaaactgt attataagta     540 aatgcatgta tactaaactc acaaattaga gcttcaattt aattatatca gttattaccc    600
gggaatctcg gtcgtaatga ttttataat gacgaaaaaa aaaaaattgg aagaaaaag     660 cttggatcca caggacgggt gtggtcgcca tgatcgcgta gtcgatagtg gctccgtccg    720
gcgtagagga tcctcaattc atcattttt ttttattctt ttttttgatt tcggtttctt    780 tgaaatttt ttgattcggt aatctccgaa cagaaggaag aacgaaggaa ggagcacaga    840
cttagattgg tatatatacg catatgtagt gttgaagaaa catgaaattg cccagtattc    900
ttaacccaac tgcacagaac aaaaacctgc aggaaacgaa gataaatcat gtcgaaagct    960
acatataagg aacgtgctgc tactcatcct agtcctgttg ctgccaagct atttaatatc   1020
atgcacgaaa agcaaacaaa cttgtgtgct tcattggatg ttcgtaccac caaggaatta   1080
ctggagttag ttgaagcatt aggtcccaaa atttgtttac taaaaacaca tgtggatatc   1140
ttgactgatt tttccatgga gggcacagtt aagccgctaa aggcattatc gccaagtac    1200 aattttttac tcttcgaaga cagaaaattt gctgacattg taatacagt caaattgcag    1260 tactctgcgg gtgtatacag aatagcagaa tgggcagaca ttacgaatgc acacggtgtg   1320
gtgggcccag gtattgttag cggtttgaag caggcggcag aagaagtaac aaaggaacct   1380
agaggccttt tgatgttagc agaattgtca tgcaagggct ccctatctac tggagaatat   1440
actaagggta ctgttgacat tgcgaagagc gacaaagatt tgttatcgg ctttattgct   1500 caaagagaca tgggtggaag agatgaaggt tacgattggt tgattatgac acccggtgtg   1560
ggtttagatg acaagggaga cgcattgggt caacagtata gaaccgtgga tgatgtggtc   1620
tctacaggat ctgacattat tattgttgga agaggactat ttgcaaaggg aagggatgct   1680
aaggtagagg gtgaacgtta cagaaaagca ggctgggaag catatttgag aagatgcggc   1740
cagcaaaact aaaaaactgt attataagta aatgcatgta tactaaactc acaaattaga   1800
gcttcaattt aattatatca gttattaccc gggaatctcg gtcgtaatga ttttataat    1860 gacgaaaaaa aaaaaattgg aagaaaaag cttggatcca caggacgggt gtggtcgcca   1920
tgatcgcgta gtcgatagtg gctcaactta gactaaggag gtttggtctg aaattactct   1980
```

-continued

```
aggtcgttac ttgttcgaaa gattaaagca agtcgaagtc caaaccatct tcggtttgcc    2040
aggtgacttc aacttgtccc tattggacaa gatctacgaa gtcccaggta tgagatgggc    2100
tggtaacgct aacgaattga acgctgctta cgctgctgat ggttacgcca gattaaaggg    2160
tatggcctgt gtcatcacca ccttcggtgt tggtgaattg tctgccttga acggtattgc    2220
cggttcttac gctgaacacg ttggtgtttt gcacgttgtt ggtaagtaag tgaggcgcgc    2280
ctgttccatc catctcttcc caagctaagc aattgttgtt gcaccacacc ttgggtaacg    2340
gtgacttcac tgttttccac agaatgtctt ccaacatttc tgaaaccact gctatgatca    2400 ctgcacatcaa cagtgctcca tctgaaatcg acagatgtat cagaaccacc tacatctctc    2460
aaagaccagt ttacttgggt ttgccagcta acttggttga cctgaaggtt ccagcttctc    2520
tattggaaac cccaattgac ttgagcttga agccaaacga cccagaagct gaaaacgaag    2580
ttctagaaac cgttttggaa ttgatcaagg acgccaagaa cccagttatc ttggccgatg    2640
cttgttgttc cagacacaac gttaaggctg aaaccaagaa gttgattgac atcactcaat    2700
tcccagcctt cgttacccca tgggtaagg gttccattga cgaacaacac caagattcg    2760 gtggtgtcta cgtcggtacc ttgcggccgc catgcaagct tggcgtaatc atggtcatag    2820
ctgtttcctg tgtgaaattg ttatccgctc acaattccac acaacatacg agccggaagc    2880
ataaagtgta aagcctgggg tgcctaatga gtgagctaac tcacattaat tgcgttgcgc    2940
tcactgcccg ctttccagtc gggaaacctg tcgtgccagc tgcattaatg aatcggccaa    3000
cgcgcgggga gaggcggttt gcgtattggg cgctcttccg cttcctcgct cactgactcg    3060
ctgcgctcgg tcgttcggct gcggcgagcg gtatcagctc actcaaaggc ggtaatacgg    3120
ttatccacag aatcagggga taacgcagga agaacatgt gagcaaaagg ccagcaaaag    3180
gccaggaacc gtaaaaaggc cgcgttgctg gcgtttttcc ataggctccg ccccctgac    3240 gagcatcaca aaaatcgacg ctcaagtcag aggtggcgaa acccgacagg actataaaga    3300
taccaggcgt ttccccctgg aagctccctc gtgcgctctc ctgttccgac cctgccgctt    3360
accggatacc tgtccgcctt tctcccttcg ggaagcgtgg cgctttctca tagctcacgc    3420
tgtaggtatc tcagttcggt gtaggtcgtt cgctccaagc tgggctgtgt gcacgaaccc    3480
cccgttcagc ccgaccgctg cgccttatcc ggtaactatc gtcttgagtc aacccggta    3540 agacacgact tatcgccact ggcagcagcc actggtaaca ggattagcag agcgaggtat    3600
gtaggcggtg ctacagagtt cttgaagtgg tggcctaact acggctacac tagaagaaca    3660
gtatttggta tctgcgctct gctgaagcca gttaccttcg gaaaaagagt ggtagctct    3720 tgatccggca acaaaccac cgctggtagc ggtggttttt ttgtttgcaa gcagcagatt    3780
acgcgcagaa aaaaggatc tcaagaagat cctttgatct tttctacggg gtctgacgct    3840
cagtggaacg aaaactcacg ttaagggatt ttggtcatga gattatcaaa aaggatcttc    3900
acctagatcc tttttaaatta aaatgaagt tttaaatcaa tctaaagtat atatgagtaa    3960
acttggtctg acagttacca atgcttaatc agtgaggcac ctatctcagc gatctgtcta    4020
tttcgttcat ccatagttgc ctgactcccc gtcgtgtaga taactacgat acgggagggc    4080
ttaccatctg gccccagtgc tgcaatgata ccgcgagacc cacgctcacc ggctccagat    4140
ttatcagcaa taaaccagcc agccggaagg gccgagcgca gaagtggtcc tgcaacttta    4200
tccgcctcca tccagtctat taattgttgc cgggaagcta gagtaagtag ttcgccagtt    4260
aatagtttgc gcaacgttgt tgccattgct acaggcatcg tggtgtcacg ctcgtcgttt    4320
ggtatggctt cattcagctc cggttcccaa cgatcaaggc gagttacatg atcccccatg    4380
```

```
ttgtgcaaaa aagcggttag ctccttcggt cctccgatcg ttgtcagaag taagttggcc    4440
gcagtgttat cactcatggt tatggcagca ctgcataatt ctcttactgt catgccatcc    4500
gtaagatgct tttctgtgac tggtgagtac tcaaccaagt cattctgaga atagtgtatg    4560
cggcgaccga gttgctcttg cccggcgtca atacgggata ataccgcgcc acatagcaga    4620
actttaaaag tgctcatcat tggaaaacgt tcttcggggc gaaaactctc aaggatctta    4680
ccgctgttga gatccagttc gatgtaaccc actcgtgcac ccaactgatc ttcagcatct    4740
tttactttca ccagcgtttc tgggtgagca aaaacaggaa ggcaaaatgc cgcaaaaaag    4800
ggaataaggg cgacacggaa atgttgaata ctcatactct tcctttttca atattattga    4860
agcatttatc agggttattg tctcatgagc ggatacatat ttgaatgtat ttagaaaaat    4920
aaacaaatag gggttccgcg cacatttccc cgaaaagtgc cacctgacgt ctaagaaacc    4980
attattatca tgacattaac ctataaaaat aggcgtatca cgaggccctt tcgtctcgcg    5040
cgtttcggtg atgacggtga aaacctctga cacatgcagc tcccggagac ggtcacagct    5100
tgtctgtaag cggatgccgg gagcagacaa gcccgtcagg gcgcgtcagc gggtgttggc    5160
gggtgtcggg gctggcttaa ctatgcggca tcagagcaga ttgtactgag agtgcaccat    5220
atgcggtgtg aaataccgca cagatgcgta aggagaaaat accgcatcag gcgccattcg    5280
ccattcaggc tgcgcaactg ttgggaaggg cgatcggtgc gggcctcttc gctattacgc    5340
cagctggcga aggggggatg tgctgcaagg cgattaagtt gggtaacgcc agggttttcc    5400
cagtcacgac gttgtaaaac gacggccagt gaattcgagc tcggtacccg gggatcctct    5460
agagtcgagc ggccgcgaag gccaccacgg ccacaaagac cacaaagacc acaaaaaaaa    5520
acaaaaaaca accgtcccag cttccagtgt ttggaatact ggaacacagg aagccgcata    5580
agagtgggcg ttgcacagga agccaggccc agaagcccca gagttacttt tttttttttg    5640
ttttttcctt ctgttcgctg tgcccgcatc agatgatgcg cctttattta cgatgccaat    5700
gcgaatagca ccagtgagag caccagtaaa agcatacgca tacacataca cacatagagc    5760
aagcaagcag gctagcaacc aggaaaggct gccagtgact gctactgggt gtctaagaac    5820
cgtagggcgg attattgttg cggtggttgg ttgcgggtgg ttatgcgatg gtacggtgca    5880
gaatcgtacg gtgttgggtt atggaattag tatgggtatg tgatatgtgg taatatgtga    5940
tattgggtta ttgtgatttg gaatactgaa tatcgaatat gggatatgga atatggctat    6000
ggcatggtat ggtatgggat gggagtattc tattttattt tattctggtt cctgcgttta    6060
gggtagggta ggaagaaggt gagtgctttt gtatataagt ggagtgtctg gatcagtttt    6120
gtggattgtg aatgttagtt tcccctttaa tgtatatttg tattatttgc ttttgagtac    6180
tcaataacca agcacaacta ctagttttaa aggatccatc ctcttaaaca gtacaaatcg    6240
caaagaaaag ctccacaccc aaaccaaata attgcaatga aactcgccgt ttatagcaca    6300
aaacagtacg acaagaagta cctgcaacag gtgaacgagt cctttggctt tgagctggaa    6360
tttttttgact ttctgctgac ggaaaaaacc gctaaaactg ccaatggctg cgaagcggta    6420
tgtattttcg taaacgatga cggcagccgc ccggtgctgg aagagctgaa aaagcacggc    6480
gttaaatata tcgccctgcg ctgtgccggt ttcaataacg tcgaccttga cgcggcaaaa    6540
gaactggggc tgaaagtagt ccgtgttcca gcctatgatc cagaggccgt tgctgaacac    6600
gccatcggta tgatgatgac gctgaaccgc cgtattcacc gcgcgtatca gcgtacccgt    6660
gatgctaact tctctctgga aggtctgacc ggctttacta tgtatggcaa aacggcaggc    6720
```

```
gttatcggta ccggtaaaat cggtgtggcg atgctgcgca ttctgaaagg ttttggtatg    6780
cgtctgctgg cgttcgatcc gtatccaagt gcagcggcgc tggaactcgg tgtggagtat    6840
gtcgatctgc aaccctgttc tctgaatca gacgttatct ctctgcactg cccgctgaca    6900
ccggaaaact atcatctgtt gaacgaagcc gccttcgaac agatgaaaaa tggcgtgatg    6960
atcgtcaata ccagtcgcgg tgcattgatt gattctcagg cagcaattga agcgctgaaa    7020
aatcagaaaa ttggttcgtt gggtatggac gtgtatgaga acgaacgcga tctattcttt    7080
gaagataaat ccaacgacgt gatccaggat gacgtattcc gtcgcctgtc tgcctgccac    7140
aacgtgctgt ttaccgggca ccaggcattc ctgacagcag aagctctgac cagtatttct    7200
cagactacgc tgcaaaactt aagcaatctg gaaaaaggcg aaacctgccc gaacgaactg    7260
gtttaa                                                               7266
```

<210> SEQ ID NO 3
<211> LENGTH: 7660
<212> TYPE: DNA
<213> ORGANISM: Kluyveromyces marxianus

<400> SEQUENCE: 3

```
ggcgcgggag attgataaga cttttctagt tgcatatctt ttatatttaa atcttatcta      60
ttagttaatt ttttgtaatt tatccttata tatagtctgg ttattctaaa atatcatttc     120
agtatctaaa aattccccctc ttttttcagt tatatcttaa caggcgacag tccaaatgtt     180
gatttatccc agtccgattc atcagggttg tgaagcattt tgtcaatggt cgaaatcaca     240
tcagtaatag tgcctcttac ttgcctcata gaatttcttt ctcttaacgt caccgtttgg     300
tcttttatag tttcgaaatc tatggtgata ccaaatggtg ttcccaattc atcgttacgg     360
gcgtattttt taccaattga agtattggaa tcgtcaattt taaagtatat ctctctttta     420
cgtaaagcct gcgagatcct cttaagtata gcggggaagc catcgttatt cgatattgtc     480
gtaacaaata ctttgatcgg cgctatctgt aatggaaacg gcgcgcctct gccgccccaa     540
tttccgtaag agttaacgct gctttgttcg atgtcgatgg tactttgatc atttcccaag     600
gtgccattgc tgaattctgg agagatttcg gtaaggacaa gccttacttc gactcccaac     660
acgttattga catttctcac ggatggagaa cctacgatgt catcaagaag tttgctccag     720
actacgctaa cgaagaatac gtcaccaagt tggaaggtga atcccagac aagtttggta     780 agcacgctat cgaagtgcca ggtgccatca agctgtgcgc tgccttgaac gctctaccta     840
aggagaagtg ggctgtcgcc acctctggta cctttgaaat ggcccacaag tggttcgata     900
tcctaggaat caagagacca tccaacttca tcacagctaa cgacgtcaag aacggtaagc     960
ctcatccaga accatacttg aagggcagaa acgtttggg ttacccaatc aacgaagcta    1020
acccgcggcc gccatgcaag cttggcgtaa tcatggtcat agctgtttcc tgtgtgaaat    1080
tgttatccgc tcacaattcc acacaacata cgagccggaa gcataaagtg taaagcctgg    1140
ggtgcctaat gagtgagcta actcacatta attgcgttgc gctcactgcc cgctttccag    1200
tcgggaaacc tgtcgtgcca gctgcattaa tgaatcggcc aacgcgcggg gagaggcggt    1260
ttgcgtattg ggcgctcttc cgcttcctcg ctcactgact cgctgcgctc ggtcgttcgg    1320
ctgcggcgag cggtatcagc tcactcaaag gcggtaatac ggttatccac agaatcaggg    1380
gataacgcag gaaagaacat gtgagcaaaa ggccagcaaa aggccaggaa ccgtaaaaag    1440
gccgcgttgc tggcgttttt ccataggctc cgcccccctg acgagcatca caaaaatcga    1500
cgctcaagtc agaggtggcg aaacccgaca ggactataaa gataccaggc gtttccccct    1560
```

```
ggaagctccc tcgtgcgctc tcctgttccg accctgccgc ttaccggata cctgtccgcc    1620 tttctcccttt cgggaagcgt ggcgctttct catagctcac gctgtaggta tctcagttcg    1680
gtgtaggtcg ttcgctccaa gctgggctgt gtgcacgaac ccccgttca gcccgaccgc     1740 tgcgccttat ccgtaactact tcgtcttgag tccaacccgg taagacacga cttatcgcca    1800
ctggcagcag ccactggtaa caggattagc agagcgaggt atgtaggcgg tgctacagag    1860
ttcttgaagt ggtggcctaa ctacggctac actagaagaa cagtatttgg tatctgcgct    1920
ctgctgaagc cagttacctt cggaaaaaga gttggtagct cttgatccgg caaacaaacc    1980
accgctggta gcggtggttt ttttgtttgc aagcagcaga ttacgcgcag aaaaaaagga    2040
tctcaagaag atcctttgat cttttctacg gggtctgacg ctcagtggaa cgaaaactca    2100
cgttaaggga ttttggtcat gagattatca aaaaggatct tcacctagat ccttttaaat    2160
taaaaatgaa gttttaaatc aatctaaagt atatatgagt aaacttggtc tgacagttac    2220
caatgcttaa tcagtgaggc acctatctca gcgatctgtc tatttcgttc atccatagtt    2280
gcctgactcc ccgtcgtgta gataactacg atacgggagg gcttaccatc tggccccagt    2340
gctgcaatga taccgcgaga cccacgctca ccggctccag atttatcagc aataaaccag    2400
ccagccggaa gggccgagcg cagaagtggt cctgcaactt tatccgcctc catccagtct    2460
attaattgtt gccgggaagc tagagtaagt agttcgccag ttaatagttt gcgcaacgtt    2520
gttgccattg ctacaggcat cgtggtgtca cgctcgtcgt ttggtatggc ttcattcagc    2580
tccggttccc aacgatcaag gcgagttaca tgatccccca tgttgtgcaa aaaagcggtt    2640
agctccttcg gtcctccgat cgttgtcaga agtaagttgg ccgcagtgtt atcactcatg    2700
gttatggcag cactgcataa ttctcttact gtcatgccat ccgtaagatg cttttctgtg    2760
actggtgagt actcaaccaa gtcattctga gaatagtgta tgcggcgacc gagttgctct    2820
tgcccggcgt caatacggga taataccgcg ccacatagca gaactttaaa agtgctcatc    2880
attggaaaac gttcttcggg gcgaaaactc tcaaggatct taccgctgtt gagatccagt    2940
tcgatgtaac ccactcgtgc acccaactga tcttcagcat cttttacttt caccagcgtt    3000
tctgggtgag caaaaacagg aaggcaaaat gccgcaaaaa agggaataag ggcgacacgg    3060
aaatgttgaa tactcatact cttcctttttt caatattatt gaagcattta tcagggttat    3120
tgtctcatga gcggatacat atttgaatgt atttagaaaa ataaacaaat aggggttccg    3180
cgcacatttc cccgaaaagt gccacctgac gtctaagaaa ccattattat catgacatta    3240
acctataaaa ataggcgtat cacgaggccc tttcgtctcg cgcgtttcgg tgatgacggt    3300
gaaaacctct gacacatgca gctcccggag acggtcacag cttgtctgta agcggatgcc    3360
gggagcagac aagcccgtca gggcgcgtca gcgggtgttg gcgggtgtcg ggctggctt     3420 aactatgcgg catcagagca gattgtactg agagtgcacc atatgcggtg tgaaataccg    3480
cacagatgcg taaggagaaa ataccgcatc aggcgccatt cgccattcag gctgcgcaac    3540
tgttgggaag ggcgatcggt gcgggcctct tcgctattac gccagctggc gaaggggga    3600 tgtgctgcaa ggcgattaag ttgggtaacg ccagggtttt cccagtcacg acgttgtaaa    3660
acgacggcca gtgaattcga gctcggtacc cggggatcct ctagagtcga gcggccgctt    3720
ctctcgtcct tcttctttc tggtgtttct tttgtcctct ggtgatgagt gagtgatatt     3780
attttcacta gtactagtac tactactact aggtttagcc ttgtttctta ttcgtagtaa    3840
aactgtgatg attcaatacc gcttcgcttc ttcttcgtct tcgtcacaca gcccaaaaat    3900
```

-continued

```
tgtcacctct tcgataattt gggcatttgg gcatccatgt attattatta tacgcatggg    3960
ggcacaagcg tgtagctaac tgttttaacc attacgctgc ttttttgatg gaataagaaa    4020
cggttggttt cgggttgccc caaataatat aaaaggacgc agttttgag tcagtgattg     4080 atttccagat gggttccgga ttattagttg atatagagtt aatagatagt atttattagt    4140
ttccttttgg taatagacca agcactagaa tttctattct acacacaaac agaaaacaca    4200
tatctatatc acaagatgaa aactgtatta taagtaaatg catgtatact aaactcacaa    4260
attagagctt caatttaatt atatcagtta ttacccggga atctcggtcg taatgatttt    4320
tataatgacg aaaaaaaaaa aattggaaag aaaaagcttg gatccacagg acgggtgtgg    4380
tcgccatgat cgcgtagtcg atagtggctc cgtccggcgt agaggatcct caattcatca    4440
tttttttttt attcttttt ttgatttcgg tttctttgaa attttttga ttcggtaatc      4500 tccgaacaga aggaagaacg aaggaaggag cacagactta gattggtata tatacgcata    4560
tgtagtgttg aagaaacatg aaattgccca gtattcttaa cccaactgca cagaacaaaa    4620
acctgcagga aacgaagata aatcatgtcg aaagctacat ataaggaacg tgctgctact    4680
catcctagtc ctgttgctgc caagctattt aatatcatgc acgaaaagca aacaaacttg    4740
tgtgcttcat tggatgttcg taccaccaag gaattactgg agttagttga agcattaggt    4800
cccaaaattt gtttactaaa aacacatgtg gatatcttga ctgattttc catggagggc     4860 acagttaagc cgctaaaggc attatccgcc aagtacaatt ttttactctt cgaagacaga    4920
aaatttgctg acattggtaa tacagtcaaa ttgcagtact ctgcgggtgt atacagaata    4980
gcagaatggg cagacattac gaatgcacac ggtgtggtgg gcccaggtat tgttagcggt    5040
ttgaagcagg cggcagaaga agtaacaaag gaacctagag gcctttgat gttagcagaa     5100 ttgtcatgca agggctccct atctactgga gaatatacta agggtactgt tgacattgcg    5160
aagagcgaca aagattttgt tatcggcttt attgctcaaa gagacatggg tggaagagat    5220
gaaggttacg attggttgat tatgacaccc ggtgtgggtt tagatgacaa gggagacgca    5280
ttgggtcaac agtatagaac cgtggatgat gtggtctcta caggatctga cattattatt    5340
gttggaagag gactatttgc aaagggaagg gatgctaagg tagagggtga acgttacaga    5400
aaagcaggct gggaagcata tttgagaaga tgcggccagc aaaactaaaa aactgtatta    5460
taagtaaatg catgtatact aaactcacaa attagagctt caatttaatt atatcagtta    5520
ttacccggga atctcggtcg taatgatttt tataatgacg aaaaaaaaaa aattggaaag    5580
aaaaagcttg gatccacagg acgggtgtgg tcgccatgat cgcgtagtcg atagtggctc    5640
aacttagact aaggaggttt ggggcgcgcc agcgtgaata atgaatggcc ttgtattcgt     5700
ttttttccga gagaaaatta acaagagcga aaaaaaaac gggcttcggt gaaaatcggg      5760
tgaatatgca actagcggga cgaatgctct ggaaatgcat atcctatgca actagcggga    5820
tgaacaaatc tcaccccaga attcgcagga aaaacagga aaaaaaaaa gaaggccacc       5880 acggccacaa agaccacaaa gaccacaaaa aaaaacaaaa aacaaccgtc ccagcttcca    5940
gtgtttggaa tactggaaca caggaagccg cataagagtg ggcgttgcac aggaagccag    6000
gcccagaagc cccagagtta ctttttttt tttgtttttt ccttctgttc gctgtgcccg      6060
catcagatga tgcgccttta tttacgatgc caatgcgaat agcaccagtg agagcaccag    6120
taaaagcata cgcatacaca tacacacata gagcaagcaa gcaggctagc aaccaggaaa    6180
ggctgccagt gactgctact gggtgtctaa gaaccgtagg gcggattatt gttgcggtgg    6240
ttggttgcgg gtggttatgc gatggtacgg tgcagaatcg tacggtgttg ggttatggaa    6300
```

```
ttagtatggg tatgtgatat gtggtaatat gtgatattgg gttattgtga tttggaatac    6360
tgaatatcga atatgggata tggaatatgg ctatggcatg gtatggtatg ggatgggagt    6420
attctatttt attttattct ggttcctgcg tttagggtag ggtaggaaga aggtgagtgc    6480
ttttgtatat aagtggagtg tctggatcag ttttgtggat tgtgaatgtt agtttcccct    6540
ttaatgtata tttgtattat ttgcttttga gtactcaata accaagcaca actactagtt    6600
ttaaaggatc catcctctta aacagtacaa atcgcaaaga aaagctccac acccaaacca    6660
aataattgca atgaaactcg ccgtttatag cacaaaacag tacgacaaga agtacctgca    6720
acaggtgaac gagtcctttg gctttgagct ggaattttt gactttctgc tgacggaaaa     6780
aaccgctaaa actgccaatg gctgcgaagc ggtatgtatt ttcgtaaacg atgacggcag    6840
ccgcccggtg ctggaagagc tgaaaaagca cggcgttaaa tatatcgccc tgcgctgtgc    6900
cggtttcaat aacgtcgacc ttgacgcggc aaaagaactg gggctgaaag tagtccgtgt    6960
tccagcctat gatccagagg ccgttgctga acacgccatc ggtatgatga tgacgctgaa    7020
ccgccgtatt caccgcgcgt atcagcgtac ccgtgatgct aacttctctc tggaaggtct    7080
gaccggcttt actatgtatg gcaaaacggc aggcgttatc ggtaccggta aaatcggtgt    7140
ggcgatgctg cgcattctga aaggttttgg tatgcgtctg ctggcgttcg atccgtatcc    7200
aagtgcagcg cgctggaac tcggtgtgga gtatgtcgat ctgccaaccc tgttctctga     7260
atcagacgtt atctctctgc actgcccgct gacaccggaa actatcatc tgttgaacga     7320 agccgccttc gaacagatga aaaatggcgt gatgatcgtc aataccagtc gcggtgcatt    7380
gattgattct caggcagcaa ttgaagcgct gaaaaatcag aaaattggtt cgttgggtat    7440
ggacgtgtat gagaacgaac gcgatctatt ctttgaagat aaatccaacg acgtgatcca    7500
ggatgacgta ttccgtcgcc tgtctgcctg ccacaacgtg ctgtttaccg gcaccaggc    7560 attcctgaca gcagaagctc tgaccagtat ttctcagact acgctgcaaa acttaagcaa    7620
tctggaaaaa ggcgaaacct gcccgaacga actggtttaa                          7660
```

<210> SEQ ID NO 4
<211> LENGTH: 7676
<212> TYPE: DNA
<213> ORGANISM: Kluyveromyces marxianus

<400> SEQUENCE: 4

```
tggccaattc cctgctaaca cacacacctc cggtatgaca tctaagacta ccattgaaat      60
caacttcaag caaatggaaa tggttatttt gggtaccgaa tatgctggtg aaatgaagaa     120
aggtatcttc accgttatgt tctatttgat gcctgtcaac cataacgtac ttaccttaca     180
ttccagtgct aaccaaggta tcactgagaa agatgttact ttgttcttcg gtttgagtgg     240
tactggtaag actaccttgt ctgctgaccc acatagactg ttgatcggtg atgatgaaca     300
ctgctggtcc gatcatggtg tcttcaacat cgaaggtggt tgctacgcca atgtctgggg     360
tttgtcagga gaaaaggaac ctgagatctt taacgccatt aggtttggtt ctgttttgga    420
aaatgtcatc tacgacccaa acaccagaga agttgattat gatgactcct caattaccga    480
aaacacaaga tgtgcttacc gcggccgcca tgcaagcttg gcgtaatcat ggtcatagct    540
gtttcctgtg tgaaattgtt atccgctcac aattccacac aacatacgag ccggaagcat    600
aaagtgtaaa gcctggggtg cctaatgagt gagctaactc acattaattg cgttgcgctc    660
actgcccgct ttccagtcgg gaaacctgtc gtgccagctg cattaatgaa tcggccaacg    720
```

```
cgcggggaga ggcggtttgc gtattgggcg ctcttccgct tcctcgctca ctgactcgct      780
gcgctcggtc gttcggctgc ggcgagcggt atcagctcac tcaaaggcgg taatacggtt      840
atccacagaa tcagggata  acgcaggaaa gaacatgtga gcaaaaggcc agcaaaaggc      900
caggaaccgt aaaaaggccg cgttgctggc gttttccat  aggctccgcc cccctgacga      960
gcatcacaaa aatcgacgct caagtcagag gtggcgaaac ccgacaggac tataaagata      1020
ccaggcgttt ccccctggaa gctccctcgt gcgctctcct gttccgaccc tgccgcttac      1080 cggataccctg tccgccttc  tcccttcggg aagcgtggcg ctttctcata gctcacgctg      1140
taggtatctc agttcggtgt aggtcgttcg ctccaagctg ggctgtgtgc acgaaccccc      1200
cgttcagccc gaccgctgcg ccttatccgg taactatcgt cttgagtcca acccggtaag      1260
acacgactta tcgccactgg cagcagccac tggtaacagg attagcagag cgaggtatgt      1320
aggcggtgct acagagttct tgaagtggtg gcctaactac ggctacacta agaacagt       1380 atttggtatc tgcgctctgc tgaagccagt taccttcgga aaaagagttg gtagctcttg      1440
atccggcaaa caaccaccg  ctggtagcgg tggttttttt gtttgcaagc agcagattac      1500
gcgcagaaaa aaaggatctc aagaagatcc tttgatcttt tctacggggt ctgacgctca      1560
gtggaacgaa aactcacgtt aagggatttt ggtcatgaga ttatcaaaaa ggatcttcac      1620
ctagatcctt ttaaattaaa aatgaagttt taaatcaatc taaagtatat atgagtaaac      1680
ttggtctgac agttaccaat gcttaatcag tgaggcacct atctcagcga tctgtctatt      1740
tcgttcatcc atagttgcct gactccccgt cgtgtagata actacgatac gggagggctt      1800
accatctggc cccagtgctg caatgatacc gcgagaccca cgctcaccgg ctccagattt      1860
atcagcaata aaccagccag ccggaagggc cgagcgcaga agtggtcctg caactttatc      1920
cgcctccatc cagtctatta attgttgccg ggaagctaga gtaagtagtt cgccagttaa      1980 tagtttcgc  aacgttgttg ccattgctac aggcatcgtg gtgtcacgct cgtcgtttgg      2040
tatggcttca ttcagctccg gttcccaacg atcaaggcga gttacatgat cccccatgtt      2100
gtgcaaaaaa gcggttagct ccttcggtcc tccgatcgtt gtcagaagta agttggccgc      2160
agtgttatca ctcatggtta tggcagcact gcataattct cttactgtca tgccatccgt      2220
aagatgcttt tctgtgactg gtgagtactc aaccaagtca ttctgagaat agtgtatgcg      2280
gcgaccgagt tgctcttgcc cggcgtcaat acgggataat accgcgccac atagcagaac      2340
tttaaaagtg ctcatcattg gaaaacgttc ttcggggcga aaactctcaa ggatcttacc      2400
gctgttgaga tccagttcga tgtaacccac tcgtgcaccc aactgatctt cagcatcttt      2460
tactttcacc agcgtttctg ggtgagcaaa aacaggaagg caaaatgccg caaaaaaggg      2520
aataagggcg acacggaaat gttgaatact catactcttc cttttcaat  attattgaag      2580 catttatcag ggttattgtc tcatgagcgg atacatattt gaatgtattt agaaaaataa      2640
acaaataggg gttccgcgca catttccccg aaaagtgcca cctgacgtct aagaaaccat      2700
tattatcatg acattaacct ataaaaatag gcgtatcacg aggcccttc  gtctcgcgcg      2760 tttcggtgat gacggtgaaa acctctgaca catgcagctc ccggagacgg tcacagcttg      2820
tctgtaagcg gatgccggga gcagacaagc ccgtcagggc gcgtcagcgg tgttggcgg      2880 gtgtcgggc  tggcttaact atgcggcatc agagcagatt gtactgagag tgcaccatat      2940
gcggtgtgaa ataccgcaca gatgcgtaag gagaaaatac cgcatcaggc gccattcgcc      3000
attcaggctg cgcaactgtt gggaagggcg atcggtgcgg gcctcttcgc tattacgcca      3060
gctggcgaaa gggggatgtg ctgcaaggcg attaagttgg gtaacgccag ggttttccca      3120
```

```
gtcacgacgt tgtaaaacga cggccagtga attcgagctc ggtacccggg gatcctctag    3180
agtcgagcgg ccgcgcaaaa ttcaccactc ggccgaacaa aatatcagaa gtgaattagg    3240
cctttctgag gaagttgtta caattagacg taatgctcca gctgctttat tgtatgaaga    3300
tgctttgaag gaaagagcca ctgcaatttc cagtgctggc gctttgattg cttactccgg    3360
tgacaaaact ggtagatcac cacgtgataa gcgtatcgtt gaagaagaga cttccaaaga    3420
taacatttgg tggggtccag taaataaacc atgttctgag agaacttggg aaatcaacag    3480
agaacgagcc gctgactact tgagaacaag agatcatatt tacattgttg atgcttacgc    3540
tggttgggac cctcgttaca gaattaaggt cagagtcgtt tgtgctagag cttaccatgc    3600
attgttcatg accaatatgt tgattagacc aacgcaagaa gagctagaaa actttggaga    3660
acctgacttc acaatttgga atgcataaat atctatatca caagatgaaa actgtattat    3720
aagtaaatgc atgtatacta aactcacaaa ttagagcttc aatttaatta tatcagttat    3780
tacccgggaa tctcggtcgt aatgattttt ataatgacga aaaaaaaaaa attggaaaga    3840
aaaagcttgg atccacagga cgggtgtggt cgccatgatc gcgtagtcga tagtggctcc    3900
gtccggcgta gaggatcctc aattcatcat tttttttttta ttcttttttt tgatttcggt    3960
ttctttgaaa tttttttgat tcggtaatct ccgaacagaa ggaagaacga aggaaggagc    4020
acagacttag attggtatat atacgcatat gtagtgttga agaaacatga aattgcccag    4080
tattcttaac ccaactgcac agaacaaaaa cctgcaggaa acgaagataa atcatgtcga    4140
aagctacata taaggaacgt gctgctactc atcctagtcc tgttgctgcc aagctattta    4200
atatcatgca cgaaaagcaa acaaacttgt gtgcttcatt ggatgttcgt accaccaagg    4260
aattactgga gttagttgaa gcattaggtc ccaaaatttg tttactaaaa acacatgtgg    4320
atatcttgac tgattttttcc atggagggca cagttaagcc gctaaaggca ttatccgcca    4380
agtacaattt tttactcttc gaagacagaa aatttgctga cattggtaat acagtcaaat    4440
tgcagtactc tgcgggtgta tacagaatag cagaatgggc agacattacg aatgcacacg    4500
gtgtggtggg cccaggtatt gttagcggtt tgaagcaggc ggcagaagaa gtaacaaagg    4560
aacctagagg ccttttgatg ttagcagaat tgtcatgcaa gggctcccta tctactggag    4620
aatatactaa gggtactgtt gacattgcga gagcgacaa agattttgtt atcggcttta    4680
ttgctcaaag agacatgggt ggaagagatg aaggttacga ttggttgatt atgacacccg    4740
gtgtgggttt agatgacaag ggagacgcat tgggtcaaca gtatagaacc gtggatgatg    4800
tggtctctac aggatctgac attattattg ttggaagagg actatttgca aagggaaggg    4860
atgctaaggt agagggtgaa cgttacagaa aagcaggctg ggaagcatat ttgagaagat    4920
gcggccagca aaactaaaaa actgtattat aagtaaatgc atgtatacta aactcacaaa    4980
ttagagcttc aatttaatta tatcagttat tacccgggaa tctcggtcgt aatgattttt    5040
ataatgacga aaaaaaaaaa attggaaaga aaaagcttgg atccacagga cgggtgtggt    5100
cgccatgatc gcgtagtcga tagtggctca acttagacta aggaggtttg ggcgcgcca    5160 gcgtgaataa tgaatggcct tgtattcgtt ttttccgag agaaaattaa caagagcgaa    5220 aaaaaaacg gcttcggtg aaaatcgggt gaatatgcaa ctagcgggac gaatgctctg    5280
gaaatgcata tcctatgcaa ctagcgggat gaacaaatct caccccagaa ttcgcaggaa    5340
aaaacaggaa aaaaaaaaag aaggccacca cggccacaaa gaccacaaag accacaaaaa    5400
aaaacaaaaa acaaccgtcc cagcttccag tgtttggaat actggaacac aggaagccgc    5460
```

```
ataagagtgg gcgttgcaca ggaagccagg cccagaagcc ccagagttac tttttttttt    5520
ttgttttttc cttctgttcg ctgtgcccgc atcagatgat gcgcctttat ttacgatgcc    5580
aatgcgaata gcaccagtga gagcaccagt aaaagcatac gcatacacat acacacatag    5640
agcaagcaag caggctagca accaggaaag gctgccagtg actgctactg ggtgtctaag    5700
aaccgtaggg cggattattg ttgcggtggt tggttgcggg tggttatgcg atggtacggt    5760
gcagaatcgt acggtgttgg gttatggaat tagtatgggt atgtgatatg tggtaatatg    5820
tgatattggg ttattgtgat ttggaatact gaatatcgaa tatgggatat ggaatatggc    5880
tatggcatgg tatggtatgg gatgggagta ttctatttta ttttattctg gttcctgcgt    5940
ttagggtagg gtaggaagaa ggtgagtgct tttgtatata agtggagtgt ctggatcagt    6000
tttgtggatt gtgaatgtta gtttccccct taatgtatat ttgtattatt tgcttttgag    6060
tactcaataa ccaagcacaa ctactagttt taaaggatcc atcctcttaa acagtacaaa    6120
tcgcaaagaa aagctccaca cccaaaccaa ataattgcaa tgaaactcgc cgtttatagc    6180 acaaacagt acgacaagaa gtacctgcaa caggtgaacg agtcctttgg ctttgagctg    6240
gaattttttg actttctgct gacggaaaaa accgctaaaa ctgccaatgg ctgcgaagcg    6300
gtatgtattt tcgtaaacga tgacggcagc cgcccggtgc tggaagagct gaaaaagcac    6360
ggcgttaaat atatcgccct cgcctgtgcc ggtttcaata acgtcgacct tgacgcggca    6420
aaagaactgg ggctgaaagt agtccgtgtt ccagcctatg atccagaggc cgttgctgaa    6480
cacgccatcg gtatgatgat gacgctgaac cgccgtattc accgcgcgta tcagcgtacc    6540
cgtgatgcta acttctctct ggaaggtctg accggcttta ctatgtatgg caaaacggca    6600
ggcgttatcg gtaccggtaa atcggtgtg gcgatgctgc gcattctgaa aggttttggt    6660
atgcgtctgc tggcgttcga tccgtatcca agtgcagcgg cgctggaact cggtgtggag    6720
tatgtcgatc tgccaacccT gttctctgaa tcagacgtta tctctctgca ctgcccgctg    6780
acaccggaaa actatcatct gttgaacgaa gccgccttcg aacagatgaa aaatggcgtg    6840
atgatcgtca ataccagtcg cggtgcattg attgattctc aggcagcaat tgaagcgctg    6900
aaaaatcaga aaattggttc gttgggtatg gacgtgtatg agaacgaacg cgatctattc    6960
tttgaagata aatccaacga cgtgatccag gatgacgtat tccgtcgcct gtctgcctgc    7020
cacaacgtgc tgtttaccgg gcaccaggca ttcctgacag cagaagctct gaccagtatt    7080
tctcagacta cgctgcaaaa cttaagcaat ctggaaaaag gcgaaacctg cccgaacgaa    7140
ctggtttaag gcgcgggaga ttgataagac ttttctagtt gcatatcttt tatatttaaa    7200
tcttatctat tagttaattt tttgtaattt atccttatat atagtctggt tattctaaaa    7260
tatcatttca gtatctaaaa attcccctct tttttcagtt atatcttaac aggcgacagt    7320
ccaaatgttg atttatccca gtccgattca tcagggttgt gaagcatttt gtcaatggtc    7380
gaaatcacat cagtaaatagt gcctcttact tgcctcatag aatttctttc tcttaacgtc    7440
accgtttggt cttttatagt ttcgaaatct atggtgatac caaatggtgt tcccaattca    7500
tcgttacggg cgtattttt accaattgaa gtattggaat cgtcaatttt aaagtatatc    7560
tctcttttac gtaaagcctg cgagatcctc ttaagtatag cggggaagcc atcgttattc    7620
gatattgtcg taacaaatac tttgatcggc gctatctgta atggaaacgg cgcgcc       7676
```

<210> SEQ ID NO 5
<211> LENGTH: 7676
<212> TYPE: DNA
<213> ORGANISM: Kluyveromyces marxianus

<400> SEQUENCE: 5

```
gcggccgcca tgcaagcttg gcgtaatcat ggtcatagct gtttcctgtg tgaaattgtt      60
atccgctcac aattccacac aacatacgag ccggaagcat aaagtgtaaa gcctggggtg     120
cctaatgagt gagctaactc acattaattg cgttgcgctc actgcccgct ttccagtcgg     180
gaaacctgtc gtgccagctg cattaatgaa tcggccaacg cgcggggaga ggcggtttgc     240
gtattgggcg ctcttccgct tcctcgctca ctgactcgct gcgctcggtc gttcggctgc     300
ggcgagcggt atcagctcac tcaaaggcgg taatacggtt atccacagaa tcaggggata     360
acgcaggaaa gaacatgtga gcaaaaggcc agcaaaaggc caggaaccgt aaaaaggccg     420
cgttgctggc gtttttccat aggctccgcc ccctgacga gcatcacaaa aatcgacgct      480
caagtcagag gtggcgaaac ccgacaggac tataaagata ccaggcgttt ccccctggaa     540
gctccctcgt gcgctctcct gttccgaccc tgccgcttac cggatacctg tccgcctttc     600
tcccttcggg aagcgtggcg ctttctcata gctcacgctg taggtatctc agttcggtgt     660
aggtcgttcg ctccaagctg ggctgtgtgc acgaaccccc cgttcagccc gaccgctgcg     720
ccttatccgg taactatcgt cttgagtcca acccggtaag acacgactta tcgccactgg     780
cagcagccac tggtaacagg attagcagag cgaggtatgt aggcggtgct acagagttct     840
tgaagtggtg gcctaactac ggctacacta agaacagt atttggtatc tgcgctctgc       900
tgaagccagt taccttcgga aaagagttg gtagctcttg atccggcaaa caaaccaccg      960
ctggtagcgg tggttttttt gtttgcaagc agcagattac gcgcagaaaa aaaggatctc    1020
aagaagatcc tttgatcttt tctacggggt ctgacgctca gtggaacgaa aactcacgtt    1080
aagggatttt ggtcatgaga ttatcaaaaa ggatcttcac ctagatcctt ttaaattaaa    1140
aatgaagttt taaatcaatc taaagtatat atgagtaaac ttggtctgac agttaccaat    1200
gcttaatcag tgaggcacct atctcagcga tctgtctatt tcgttcatcc atagttgcct    1260
gactccccgt cgtgtagata actacgatac gggagggctt accatctggc cccagtgctg    1320
caatgatacc gcgagaccca cgctcaccgg ctccagattt atcagcaata accagccag     1380
ccggaagggc cgagcgcaga agtggtcctg caactttatc cgcctccatc cagtctatta    1440
attgttgccg ggaagctaga gtaagtagtt cgccagttaa tagtttgcgc aacgttgttg    1500
ccattgctac aggcatcgtg gtgtcacgct cgtcgtttgg tatggcttca ttcagctccg    1560
gttcccaacg atcaaggcga gttacatgat cccccatgtt gtgcaaaaaa gcggttagct    1620
ccttcggtcc tccgatcgtt gtcagaagta agttggccgc agtgttatca ctcatggtta    1680
tggcagcact gcataattct cttactgtca tgccatccgt aagatgcttt tctgtgactg    1740
gtgagtactc aaccaagtca ttctgagaat agtgtatgcg gcgaccgagt tgctcttgcc    1800
cggcgtcaat acgggataat accgcgccac atagcagaac tttaaaagtg ctcatcattg    1860
gaaaacgttc ttcggggcga aaactctcaa ggatcttacc gctgttgaga tccagttcga    1920
tgtaacccac tcgtgcaccc aactgatctt cagcatcttt tactttcacc agcgtttctg    1980
ggtgagcaaa aacaggaagg caaaatgccg caaaaaaggg aataagggcg acacggaaat    2040
gttgaatact catactcttc ctttttcaat attattgaag catttatcag ggttattgtc    2100
tcatgagcgg atacatattt gaatgtattt agaaaaataa acaaataggg gttccgcgca    2160
catttccccg aaaagtgcca cctgacgtct aagaaaccat tattatcatg acattaacct    2220
ataaaaatag gcgtatcacg aggccctttc gtctcgcgcg tttcggtgat gacggtgaaa    2280
```

```
acctctgaca catgcagctc ccggagacgg tcacagcttg tctgtaagcg gatgccggga    2340
gcagacaagc ccgtcagggc gcgtcagcgg gtgttggcgg gtgtcggggc tggcttaact    2400
atgcggcatc agagcagatt gtactgagag tgcaccatat gcggtgtgaa ataccgcaca    2460
gatgcgtaag gagaaaatac cgcatcaggc gccattcgcc attcaggctg cgcaactgtt    2520
gggaagggcg atcggtgcgg gcctcttcgc tattacgcca gctggcgaaa ggggatgtg     2580 ctgcaaggcg attaagttgg gtaacgccag ggttttccca gtcacgacgt tgtaaaacga    2640
cggccagtga attcgagctc ggtacccggg gatcctctag agtcgagcgg ccgcacaagc    2700
atctaatggc tgctgttgcc cgtaacagca gcagagcttt gaacgtttct gctcgctctg    2760
gcaccaccgc cagattgttt tctacatcaa gaccagcctt caatgctgct gctggtaagc    2820
cttccttggc caagagagtt ttgaagggta ctttgaaaac ctctttggtt gccttgcttg    2880
caggtactgc ttatgtctct tatgaattat acagggaggc taacccacct ccacaagttc    2940
cacaatctcc aactttcagc aatggatctc aagaaagac cctagtcgtc ttgggtaccg     3000
gttggggttc cgtctcgcta ttgaagaact tggacaccac cttgtacaac gttattgtcg    3060
tttctccaag aaactacttt ttgttcactc ccttattgcc atctaccccc gtcggtactg    3120
ttgaattgaa gtctattgtc caacctgtta gaactatcac cagatcttcc ccaggtgaag    3180
tccaataaat atctatatca caagatgaaa actgtattat aagtaaatgc atgtatacta    3240
aactcacaaa ttagagcttc aatttaatta tatcagttat tacccgggaa tctcggtcgt    3300
aatgattttt ataatgacga aaaaaaaaaa attggaaaga aaaagcttgg atccacagga    3360
cgggtgtggt cgccatgatc gcgtagtcga tagtggctcc gtccggcgta gaggatcctc    3420
aattcatcat ttttttttta ttcttttttt tgatttcggt ttctttgaaa ttttttttgat    3480 tcggtaatct ccgaacagaa ggaagaacga aggaaggagc acagacttag attggtatat    3540
atacgcatat gtagtgttga agaaacatga aattgcccag tattcttaac ccaactgcac    3600
agaacaaaaa cctgcaggaa acgaagataa atcatgtcga aagctacata taaggaacgt    3660
gctgctactc atcctagtcc tgttgctgcc aagctattta atatcatgca cgaaaagcaa    3720
acaaacttgt gtgcttcatt ggatgttcgt accaccaagg aattactgga gttagttgaa    3780
gcattaggtc ccaaaatttg tttactaaaa acacatgtgg atatcttgac tgattttcc     3840 atggagggca cagttaagcc gctaaaggca ttatccgcca agtacaattt tttactcttc    3900
gaagacagaa aatttgctga cattggtaat acagtcaaat tgcagtactc tgcgggtgta    3960
tacagaatag cagaatgggc agacattacg aatgcacacg gtgtggtggg cccaggtatt    4020
gttagcggtt tgaagcaggc ggcagaagaa gtaacaaagg aacctagagg ccttttgatg    4080
ttagcagaat tgtcatgcaa gggctccta tctactggag aatatactaa gggtactgtt     4140
gacattgcga agagcgacaa agattttgtt atcggcttta ttgctcaaag agacatgggt    4200
ggaagagatg aaggttacga ttggttgatt atgacacccg gtgtgggttt agatgacaag    4260
ggagacgcat tgggtcaaca gtatagaacc gtggatgatg tggtctctac aggatctgac    4320
attattattg ttggaagagg actatttgca aagggaaggg atgctaaggt agagggtgaa    4380
cgttacagaa agcaggctg ggaagcatat ttgagaagat gcggccagca aaactaaaaa     4440
actgtattat aagtaaatgc atgtatacta aactcacaaa ttagagcttc aatttaatta    4500
tatcagttat tacccgggaa tctcggtcgt aatgattttt ataatgacga aaaaaaaaa     4560 attggaaaga aaaagcttgg atccacagga cgggtgtggt cgccatgatc gcgtagtcga    4620
tagtggctca acttagacta aggaggtttg gggcgcgcca gcgtgaataa tgaatggcct    4680
```

```
tgtattcgtt tttttccgag agaaaattaa caagagcgaa aaaaaaaacg ggcttcggtg    4740
aaaatcgggt gaatatgcaa ctagcgggac gaatgctctg gaaatgcata tcctatgcaa    4800
ctagcgggat gaacaaatct caccccagaa ttcgcaggaa aaacaggaa aaaaaaaag     4860 aaggccacca cggccacaaa gaccacaaag accacaaaaa aaaacaaaaa acaaccgtcc    4920
cagcttccag tgtttggaat actggaacac aggaagccgc ataagagtgg gcgttgcaca    4980
ggaagccagg cccagaagcc ccagagttac ttttttttt ttgttttttc cttctgttcg     5040
ctgtgcccgc atcagatgat gcgcctttat ttacgatgcc aatgcgaata gcaccagtga    5100
gagcaccagt aaaagcatac gcatacacat acacacatag agcaagcaag caggctagca    5160
accaggaaag gctgccagtg actgctactg ggtgtctaag aaccgtaggg cggattattg    5220
ttgcggtggt tggttgcggg tggttatgcg atggtacggt gcagaatcgt acggtgttgg    5280
gttatggaat tagtatgggt atgtgatatg tggtaatatg tgatattggg ttattgtgat    5340
ttggaatact gaatatcgaa tatgggatat ggaatatggc tatggcatgg tatggtatgg    5400
gatgggagta ttctatttta ttttattctg gttcctgcgt ttagggtagg gtaggaagaa    5460
ggtgagtgct tttgtatata agtggagtgt ctggatcagt tttgtggatt gtgaatgtta    5520
gtttccccct taatgtatat ttgtattatt tgcttttgag tactcaataa ccaagcacaa    5580
ctactagttt taaaggatcc atcctcttaa acagtacaaa tcgcaaagaa aagctccaca    5640
cccaaaccaa ataattgcaa tgaaactcgc cgtttatagc acaaaacagt acgacaagaa    5700
gtacctgcaa caggtgaacg agtcctttgg ctttgagctg gaattttttg actttctgct    5760
gacggaaaaa accgctaaaa ctgccaatgg ctgcgaagcg gtatgtattt tcgtaaacga    5820
tgacggcagc cgcccggtgc tggaagagct gaaaaagcac ggcgttaaat atatcgccct    5880
gcgctgtgcc ggtttcaata acgtcgacct tgacgcggca aaagaactgg ggctgaaagt    5940
agtccgtgtt ccagcctatg atccagaggc cgttgctgaa cacgccatcg gtatgatgat    6000
gacgctgaac cgccgtattc accgcgcgta tcagcgtacc cgtgatgcta acttctctct    6060
ggaaggtctg accggctta ctatgtatgc aaaacggca ggcgttatcg gtaccggtaa     6120
aatcggtgtg gcgatgctgc gcattctgaa aggttttggt atgcgtctgc tggcgttcga    6180
tccgtatcca agtgcagcgg cgctggaact cggtgtggag tatgtcgatc tgccaaccct    6240
gttctctgaa tcagacgtta tctctctgca ctgcccgctg acaccggaaa actatcatct    6300
gttgaacgaa gccgccttcg aacagatgaa aaatggcgtg atgatcgtca ataccagtcg    6360
cggtgcattg attgattctc aggcagcaat tgaagcgctg aaaaatcaga aaattggttc    6420
gttgggtatg gacgtgtatg agaacgaacg cgatctattc tttgaagata aatccaacga    6480
cgtgatccag gatgacgtat tccgtcgcct gtctgcctgc acaacgtgc tgtttaccgg     6540 gcaccaggca ttcctgacag cagaagctct gaccagtatt tctcagacta cgctgcaaaa    6600
cttaagcaat ctgaaaaag gcgaaacctg cccgaacgaa ctggtttaag cgcgggaga    6660 ttgataagac ttttctagtt gcatatcttt tatatttaaa tcttatctat tagttaattt    6720
tttgtaattt atccttatat atagtctggt tattctaaaa tatcatttca gtatctaaaa    6780
attcccctct tttttcagtt atatcttaac aggcgacagt ccaaatgttg atttatccca    6840
gtccgattca tcagggttgt gaagcatttt gtcaatggtc gaaatcacat cagtaatagt    6900
gcctcttact tgcctcatag aatttctttc tcttaacgtc accgtttggt ctttatagt     6960 ttcgaaatct atggtgatac caaatggtgt tcccaattca tcgttacggg cgtatttttt    7020
```

```
accaattgaa gtattggaat cgtcaatttt aaagtatatc tctcttttac gtaaagcctg    7080
cgagatcctc ttaagtatag cggggaagcc atcgttattc gatattgtcg taacaaatac    7140
tttgatcggc gctatctgta atggaaacgg cgcgccctac tacgaagctg aagccaagga    7200
tgtcgaccct gttgccaaga ccgtcagaat caagtctgct accaaggacc acgattacga    7260
attggacttg aagtacgact acttggtcgt cggtgtcggt gctcagccaa ctacctttgg    7320
tatcccaggt gtgtttgaaa atgcttcctt cttgaaggaa atccctgacg ctcaagacat    7380
tagaactaag atcatgaaca acatcgaaaa ggccgctacc ctatctccaa atgacccaga    7440
acgtaagaga ttgttgagct tgttgttgt tggtggtggt ccaaccggtg ttgaattcgc    7500
tgctgaattg caagactacg ttgaccaaga tttgtctaaa tggatcccag aaatctctaa    7560
agaaattaag gtcactttgg ttgaagctct tccaaacatt ttgaacatgt tcgacaagtc    7620
tctatggcaa tacgcccaag atttgttcgc taaggaaaag attgacttga aattgc        7676

<210> SEQ ID NO 6
<211> LENGTH: 2883
<212> TYPE: DNA
<213> ORGANISM: Kluyveromyces marxianus

<400> SEQUENCE: 6
tgcttgcgct gctcctgcta gaaatccaga ccttaagtag tcaaacaaat tgtgttgaaa      60
agctggctcc actgatctga ctgggaaatt attcagggta gtcaagtatg tggtataaag     120
aactacccca gcaagggaat ttgccaccaa aggaggcaat attctatcag gaataacttt     180
ccacccatac ttatttagtg ccttagtaac tattccaatg gaggaatttt cgaagtagta     240
tgtatatttg ggactccaaa acttatattt tgaacgtcgt accttagaat ccttatttgt     300
atcatcactc ccagtcaaca gtactcgaat ataatgcgta tagtcaaatc tggccggtcg     360
aaacagtttt aatggagttc tcatatagaa tgaagtcatc tgataaacca tagatcttcc     420
accagcagtt aaagcaccaa caagtgacga attctgattg gaaagaccat tctgctttac     480
ttttagagca tcttggtctt ctgagctcat tataccctcaa tcaaaactga aattaggtgc     540
ctgtcacggc tcttttttta ctgtacctgt gacttccttt cttatttcca aggatgctca     600
tcacaatacg cttctagatc tattatgcat tataattaat agttgtagct acaaaaggta     660
aaagaaagtc cggggcaggc aacaatagaa atcggcaaaa aaaactacag aaatactaag     720
agcttcttcc ccattcagtc atcgcatttc gaaacaagag gggaatggct ctggctaggg     780
aactaaccac catcgcctga ctctatgcac taaccacgtg actacatata tgtgatcgtt     840
tttaacattt ttcaaaggct gtgtgtctgg ctgtttccat taattttcac tgattaagca     900
gtcatattga atctgagctc atcaccaaca agaaatacta ccgtaaaagt gtaaaagttc     960
gtttaaatca tttgtaaact ggaacagcaa gaggaagtat catcagctag ccccataaac    1020
taatcaaagg aggatgtcga ctaagagtta ctcggaaaga gcagctgctc atagaagtcc    1080
agttgctgcc aagcttttaa acttgatgga agagaagaag tcaaacttat gtgcttctct    1140
tgatgttcgt aaaacagcag agttgttaaa attagtcgag gttttgggtc catatatctg    1200
tctattgaag acacatgtag atatcttgga ggatttcagc tttgagaata ccattgtgcc    1260
gttgaagcaa ttagcagaga acacaagtt tttgatattt gaagacagga agtttgccga    1320
cattgggaac actgttaaat tacaatacac gtctggtgta taccgtatcg ccgaatggtc    1380
tgatatcacc aatgcacacg gtgtgactgg tgcgggcatt ttgctggtt tgaagcaagg    1440 tgccgaggaa gttacgaaag aacctagagg gttgttaatg cttgccgagt tatcgtccaa    1500
```

-continued

```
ggggtctcta gcgcacggtg aatacactcg tgggaccgtg gaaattgcta agagtgataa    1560
ggactttgtt attggattta ttgctcaaaa cgatatgggt ggaagagaag agggctacga    1620
ttggttgatc atgacgccag gtgttggtct tgatgacaaa ggtgatgctt tgggacaaca    1680
atacagaact gtggatgaag ttgttgccgg tggatcagac atcattattg ttggtagagg    1740
tcttttcgca aagggaagag atcctgtagt ggaaggtgag agatacagaa aggcgggatg    1800
ggacgcttac ttgaagagag taggcagatc cgcttaagag ttctccgaga acaagcagag    1860
gttcgagtgt actcggatca gaagttacaa gttgatcgtt tatatataaa ctatacagag    1920
atgttagagt gtaatggcat tgcgcacatt gtatacgcta caagtttagt cacgtgctag    1980
aagctgtttt ttgcaccgaa aattttttt tttttttttt tttgtttttt ggtgaagtac    2040
attatgtgaa atttcacaac caaagaaaaa gagtttaata caagtgcgaa gaaccaaacc    2100
ttgcttctta gtccattgac cgttataaaa gatacacatt tctgctagac tttctgcttt    2160
actactagtg tgaagaaaga tacaagagtc aattttatt gagtcttgga ccgtcgattg    2220
ctagaacaaa aaaatcaaat acacagttaa aaatggatca actaaatggt aaggaacaac    2280
aagagttcca aagaattgtg gaacaaaagc aaatgaagga cttcatgcgt ctatactcca    2340
acttggtcga aagatgtttc agtgactgtg tcaacgactt tacctctgct aagctaactt    2400
ccaaggagca aagctgcata atgaaatgct cagaaaagtt cttgaaacat agtgaacgtg    2460
ttggacaacg tttccaagag caaaacgctg ctttgaacca aagcatgggt cgttaagtta    2520
tacaaacagt tatgatataa atagttatag cttttctctct gtatatagcc aatatagcta    2580
ctaatagttc acataaacaa gtgctgcacg atgtgtaaag gaacttatct ataatagatt    2640
tcaaatatca accactacta ctcactatac tcagtgatgg ccgatgtcat aagaatcgct    2700
aatataaatt aataggcgaa tgcacaagaa gcataccaag aaaataaaag ttgaaggaaa    2760
aagagagaat ttagatctcc tcagacacca agtaatcggt attgtgttac ctgcaaaccg    2820
ataaatcggt gttgcagact ctctgcattg cactcaacta ggccttgcct ctatgaagag    2880
gtc                                                                 2883
```

MICROORGANISMS AND PROCESSES FOR LACTIC ACID PRODUCTION

CROSS-REFERENCE TO RELATED APPLICATIONS

This application claims the priority of the U.S. Provisional Application Ser. No. 62/631,541, filed on Feb. 16, 2018.

FIELD OF THE INVENTION

The invention relates to the field of genetic engineering of microorganisms for chemical production. More specifically, the invention relates to the production of lactic acid from renewable carbon resources using genetically modified yeasts.

BACKGROUND OF THE INVENTION

Many of the plastics and fibers in current usage are poorly compostable in the natural environment; for example, plastics and fibers derived from polyethylene, polypropylene, polycarbonates, polyesters and nylons remain in the natural environments for a very long time. For the purpose of long-term environmental stewardship, it is desirable to replace traditional plastics and fibers with polymers derived from bio-renewable resources which are easily compostable in the natural environments. Furthermore, as the world's supply of mined petroleum becomes scarcer and more expensive to obtain, it is desirable to replace petrochemical monomers with bio-renewable monomers. Polymers of lactic acid are generally compostable in the natural environments. Lactic acid (2-hydroxy propanoic acid) exists as either of two sterioisomers, L-lactic acid, also known as L(+)-lactic acid or S-lactic acid (L-LAC), or D-lactic acid, also known as D(−)-lactic acid or R-lactic acid (D-LAC). Both isomers can be made from bio-renewable resources, such as sugars, by fermentation. Most of the lactic acid currently produced by fermentation is L-LAC. Poly-L-lactic acid (PLLA) is biodegradable and makes plastics that are useful for some applications; however, its relatively low melting temperature of about 180° C. limits its usefulness (Tsuji, 2005). However, the melting temperature of PLLA can be raised by about 45° C. to about 225° C. by melting together equal weights of PLLA and poly-D-lactic acid (PDLA) to give what is referred to herein as a "stereocomplex PLA" (Tsuji, 2005).

Raising the melting temperature to above the boiling point of water is important for many applications, such as cups for hot drinks, plastic eating utensils and fabrics that can be washed and ironed or pressed at hot temperatures. Most importantly, the higher melting temperature of stereocomplex PLA is necessary for producing high quality "fracking beads", which are pumped into fractured rock formations in deep gas and oil deposits for the purpose of keeping the cracks open enough to extract, remove, or pump out the desired gas or oil.

Lactic acid can be polymerized starting from the free acid or from a lactide. A lactide is a cyclic diester of lactic acid, and can be comprised of two molecules of L-LAC (L,L-lactide), two molecules of D-LAC (D,D-lactide), or one molecule each of L-LAC and D-LAC (D,L-lactide or meso-lactide). Polymerizing a mixture of L-lactic acid and D-lactic acid monomers, or a mixture of lactides (L,L-lactide, D,D-lactide and D,L-lactide) does not lead to a polymer with the desired higher melting temperature (Tsuji, 2005). Instead, in order to obtain the desired polymer with a higher melting temperature, high molecular weight polymers of highly pure L-LAC and highly pure D-lactic acid must be made separately, and mixed only after polymerization. Thus, in order to make the desirable and useful stereocomplex PLA, the starting materials must be pure chiral L-LAC and pure chiral D-LAC. Sometimes the pure isomers are referred to as "optically pure." "Optically pure" or "pure chiral" as used herein means that the lactic acid is greater than 99% of one isomer by weight or mole percent. Optical purity can be determined by any one of well-known methods, for example analytical high pressure liquid chromatography (HPLC) using a column that is packed with a medium that itself carries an optically pure chiral component on its surface, for example a Phenomenex (Torrance, Calif., USA) Chirex 3126 column (250×4.60 mm) that is packed with beads coated with D-penicillamine. The mobile phase is aqueous 1 mM copper sulfate with a flow rate of 1 ml/minute and UV detection at 254 nm. An alternative method uses a Shodex™ ORpak CRX-853 (8.0 mm I.D.×50 mm) column (Showa Denko, Tokyo, Japan), eluted with aqueous 0.5 mM $CuSO_4$, a flow rate 1.0 mL/min, detection with 1N at 230 nm, and column temperature 50° C., as recommended by the manufacturer. If the isomer of lactic acid is not specified in a particular context, then the term "lactic acid" or "lactate" refers to either or both isomers, or a mixture of the two. Lactic acid produced by non-biological chemical synthesis is a racemic mixture of equal portions of L-LAC and D-LAC, so it cannot be used to make stereocomplex PLA.

Historically, most lactic acid manufactured on a large scale has been L-LAC, if produced biologically by fermentation with a micro-organism, or a racemic mixture of L-LAC and D-LAC, if produced chemically (i.e., non-biologically). A process was developed for producing highly pure chiral D-LAC by a genetically engineered strain of *Escherichia coli* (Zhou et al., 2003). However, since *E. coli* only grows well at neutral pH, the D-LAC must be produced as a salt (for example with the ammonium, sodium, potassium, calcium, or magnesium cation), and then the protonated free acid must be separated from the cation to enable polymerization, which adds significant cost to the process. As of Nov. 28, 2017, D-LAC, produced by an undisclosed process, can be purchased from the Purac division of Corbion (Amsterdam, Netherlands). However, the purchase price for D-LAC is significantly higher than that of L-LAC. As a result of the high price of pure D-LAC, stereocomplex PLA has not been widely adopted by large-scale commercial producers.

US Patent Application Publication No. US 2015/0152449 discloses a chemical process for producing D-LAC from either L-LAC or a racemic mixture of L-LAC and D-LAC. This process involves first making a racemic mixture by heating L-LAC. The racemic lactide mix is then dissolved in n-butanol and acetone, and passed over a column of immobilized Novozyme 435 (MilliporeSigma, St. Louis, Mo., USA), which is a lipase enzyme that is stereospecific for ester formation. The product is a 50-50 mix of the 1-butanol ester of D-lactic acid and the 1-butanol ester of L,L-lactyllactic acid (dimer). These two chemicals can then be separated by distillation and presumably hydrolyzed to give free acid, lactide, and or polymer, although this US patent application Publication did not disclose how this last step is done. The yield and purity from the enzymatic and distillation processes were not perfect. In one example, the yield of D-butyl lactate fell from 92% to 79% after 8 runs of 7 hours each over the immobilized enzyme. In one example of the separation of the two esters by distillation, "the distilled product analyzed was 93.9% (R)-butyl lactate; 0.4% (S)-butyl lactate, 5.0% butanol; 0.5% (S,S)-butyl lactyllactate; 0.1% (R,R)-butyl lactyllactate and 0.1% (R,R)-lactide." As such, the lactic ester portion contained about 99% D-LAC and about 1% L-LAC. It was not shown in this US patent application Publication whether that level of purity is sufficient to make high quality stereocomplex PLA. In any case, the process disclosed in this US patent application Publication is rather complicated, requires several unit operations (in addition to fermentation and downstream purification), an expensive enzyme that might have a limited lifetime, and explosion-proof equipment, and is therefore likely to be more costlier than a simple fermentation process for producing isomeric form of lactic acid in a pure form.

Thus, there remains a need for a process to produce optically pure D-LAC in order to encourage wider adoption of stereocomplex PLA as an economically attractive compostable plastic.

One approach to reducing the cost of producing D-LAC is to use a yeast as the production organism. Many yeast strains can grow well compared to most bacteria at a relatively low pH, so it is possible that D-LAC or L-LAC can be produced by fermentation at a pH that is at or below its pKa, which is published to be pH 3.86. At pH 3.86, only about half as much cation is required compared to a pH 7 fermentation, so that the downstream processing to separate the cations will be commensurately less expensive. If the final pH in the production fermentor can be even lower than 186, then production cost can be reduced even further.

There is much prior art in the field of L-lactate production by yeasts, but there is much less prior art in the field of D-lactate production (see Sauer et al, 2010 for a comprehensive review).

Zhou et al disclose increased production of D-LAC by genetically engineered *E. coli*, which naturally produces D-LAC, in which competing anaerobic pathways were deleted, and metabolic evolution was applied (Zhou et al, 2003; U.S. Pat. Nos. 7,629,162 and 8,426,191). Dequin and Bane (1994) introduced the concept of engineering the yeast *Saccharomyces cerevisiae*, which does not naturally produce either L-LAC or D-LAC, to produce L-LAC by introducing an L-lactate dehydrogenase, but the resulting yeast still produced ethanol. Porro et al (1995) expanded the concept of producing L-LAC without ethanol from yeast by introducing an L-LAC dehydrogenase and blocking the ethanol pathway by deleting one or more genes that encode pyruvate decarboxylase. Porro et al also introduced the concept of using yeasts from genera other than *Saccharomyces*, such as *Kluyveromyces, Torulopsis*, and *Zygosaccharomyces* (U.S. Pat. Nos. 6,429,006 B1, 7,049,108 B2 and 7,326,550). Rajgarhia et al introduced the concept of blocking the glycerol biosynthetic pathway and using Crabtree negative yeasts from genera other than *Saccharomyces*, including *Kluyveromyces, Pichia*, and *Hansenula*, for L-LAC production (U.S. Pat. Nos. 6,485,947 and 7,141,410).

A Crabtree positive yeast strain (for example many *S. cerevisiae* strains) is a strain that produces ethanol and carbon dioxide by the "anaerobic" or "fermentative" pathway from a fermentable carbon source such as glucose or other suitable sugar, even in the presence of air oxygen when the concentration of sugar is above about 5 g/L. A Crabtree negative yeast strain (for example many *K. marxianus* and *K. lactis* strains) is a strain that does not produce ethanol and carbon dioxide by the "anaerobic" or "fermentative" pathway from a fermentable carbon source such as glucose or other suitable sugar in the presence of air oxygen when the concentration of sugar is above about 5 g/L.

Whether a strain is Crabtree positive or negative can be determined by the method of van Dijken using submerged inverted Durham tubes in a rich medium containing 2% glucose, and determining accumulation of gas (carbon dioxide) in the inverted Durham tube after aerobic incubation (van Dijken et al, 1986). Crabtree positive strains produce gas, which visibly collects in the inverted Durham tube, while Crabtree negative strains do not.

There are few disclosures on the topic of D-LAC production at low pH by engineered yeasts. A "low pH" is defined as a pH below the published pKa for D-lactic acid or L-lactic acid, which is 3.86. Winkler introduced the concept of producing D-lactic acid using yeast and showed the production of D-LAC at 37 g/L D-LAC with an average specific productivity of 0.54 g/L-hour by an engineered *S. cerevisiae* strain (US Patent Application Publication No. 2007/0031950). Miller et al produced D-LAC from an engineered *K. marxianus* strain with a specific productivity of 0.58 g/L-hour and a yield of 0.69 g/g from a medium starting with 90 g/L glucose and ending at pH 3.0, but titers and times were not given, so one can only infer a maximum titer of 62 g/L and a fermentation time of at least 107 hours, assuming all glucose was used, and depending on the volume of KOH solution added (U.S. Pat. No. 8,137,953). Yocum et al. discloses an engineered strain of *K. marxianus* that produced D-LAC at 49 g/L in 48 hours for an average specific productivity of 1.02 g/L-hour (US Patent Application No. 2015/0240270). However, none of the prior art discloses a strain and processes for producing D-LAC at a low pH in the final fermentation broth that would be economically attractive.

Baek et al (2016) discloses an engineered and evolved strain of *S. cerevisiae* that produced 112 g/L D-LAC in 52 hours with a yield of 0.80 g/g glucose, and a specific productivity of 2.2 g/L-hr. However to achieve these parameters, the authors used a rich medium, YPD (yeast extract, peptone, dextrose), and calcium carbonate for neutralization, both features that are not desirable. The rich medium is costly upfront and adds to the downstream purification costs. Fermentation at neutral pH negates the advantage of using yeast as a production organism. The same group (Baek et al, 2017) discloses further engineered and evolved strains of *S. cerevisiae* that produced 82.6 g/L D-LAC at pH 3.5 with yield of 0.83 g/g glucose in 55 hours, for a specific productivity of 1.50 g/L-hr. However, traces of ethanol were still produced and a rich medium, (YPD medium containing yeast extract, peptone, dextrose) was used, which, as mentioned above, is undesirable for economic reasons. Another Korean group (PCT/KR2015/006225; Bae et al, 2018) discloses production of either L-LAC or D-LAC from engineered *K. marxianus* strains, using glucose or Jerusalem artichoke powder as carbon sources. L-LAC was produced at 130 g/L with a yield of 0.98 in 66 hours. D-LAC was produced at 122 g/L with a yield of 0.95 in 66 hours. However, in both cases, the pH was maintained at 6.0 with NaOH, and the cells were pre-grown to high density in a rich medium (YPD medium containing yeast extract, peptone, dextrose) and concentrated by centrifugation before inoculating the production fermentor. This practice is impractical and too expensive to be used commercially. Furthermore, as mentioned above, fermenting at a pH that is substantially higher than the pKa of lactic acid negates the advantage of using a yeast. Kim et al. (U.S. Pat. No. 9,353,388) disclose overexpression of lactic acid transporters encoded by JEN1 and ADY2 in *S. cerevisiae*, however the highest L-LAC titer reported was 13.3 g/L, and no details on fermentation conditions were given. Table 1 of the instant patent application summarizes the most relevant prior art references by listing the best published processes for producing L-LAC and D-LAC by fermentation using a yeast strain wherein the final pH is at or below the published pKa for lactic acid.

Production of commodity chemicals by fermentation at a cost that is competitive with chemicals produced from petroleum is difficult. The petrochemical industry has been active for more than 100 years, and highly developed technology now exists for producing useful chemicals at a large scale, including fuels and monomers for polymers, such as ethylene, propylene, butadiene, isoprene, ethylene glycol, terephthallic acid, adipic acid, hexamethylene diamine, caprolactam, and many others. Historically, very few commodity chemicals have been produced by fermentation and the only large volume examples have been ethanol, L-LAC, citric acid, succinic acid, itaconic acid, and couple of the L-amino acids. There are three highly significant problems with producing chemicals by fermentation. First, the raw product is mostly in water, and the water must be separated from the desired chemical, which is energy intensive and costly. Second, if the chemical is to be used for polymerization, it must be extremely pure in order to prevent chain termination, unwanted coloration, and catalyst poisoning. Microbes typically produce a wide variety of chemicals in addition to the desired product, so these unwanted contaminants must be purified away. Many microbes grow better in a rich medium that contains many nutrients, for example molasses, peptone, Jerusalem artichoke powder, or yeast extract (as opposed to a minimal or chemically defined medium), but rich media are relatively expensive and contain many impurities that remain in the fermentation broth and therefore need to be purified away as well. Third, at the titers required for attractive economics, the desired chemicals are usually toxic to the cells, which limits titers and productivity. Thus, it is quite difficult to profitably produce commodity chemicals by fermentation.

With the advent of genetic engineering, it seemed possible that many more commodity chemicals could be profitably produced, because the producing microbes could be manipulated much more easily and drastically than in the past using classical strain development methods. However, in reality, only a few new commodity chemicals have been successfully produced in commercial scale since the advent of genetic engineering, for example 1,3-propane diol. Several other chemicals have been attempted, but most with only limited success, primarily due to price competition from petrochemicals, for example succinic acid, isoprene, 1,4-butane diol, and isobutanol.

Thus, there is still a need for improved microbes and fermentation processes for producing commodity chemicals such as D-LAC and L-LAC, in which the myriad of problems mentioned above are solved to the point that economically attractive processes may be commercialized. The focus of this invention is to provide such microbes and fermentation processes.

SUMMARY OF THE INVENTION

This invention relates generally to production of D-lactic acid and/or L-lactic acid by fermentation at titers, yields, pH and times that result in an economically attractive process.

The inventors of the invention believe that wide adoption of stereocomplex PLA would require a D-LAC selling at a price of no more than twice the current price of L-LAC. Although it is impossible to pick a particular selling price for L-LAC, since its price varies widely depending on time, place, volume, and purity, it is likely that D-LAC will have to be produced at greater than 90 g/L, in less than 48 hours, at a yield greater than 0.75 g/g, and at a pH of less than 3.86, with an average specific productivity of greater than 1.875 g/L-hr. Disclosed herein are strains and fermentation processes that meet these parameters, where no such strain or process has been disclosed in the prior art.

The prior art discloses that it is theoretically impossible to produce an organic acid such as D-LAC by fermentation at high yield and at low pH under anaerobic or microaerobic conditions because the cell would have to expend all available energy (for example in the form of ATP) to export the acid and keep the acid outside of the cell (van Maris et al, 2004). Thus, it was surprising that the inventors were able to construct yeast strains that could produce D-LAC at high titers and low pH under microaerobic conditions.

Unless otherwise defined, all technical and scientific terms used herein have the same meaning as commonly understood by a person having ordinary skill in the art. Although methods and materials similar or equivalent to those described herein can be used in the practice or testing of the invention, suitable methods and materials are described below. All publications, patent applications, patents, and other references mentioned are hereby incorporated by reference in their entirety. In case of conflict, the specification, including definitions provided in the instant patent application will control.

Other features, structures, components, or characteristics as well as the advantages of the invention will be apparent from the description of the invention.

DETAILED DESCRIPTION OF THE PREFERRED EMBODIMENTS

Figure 1:
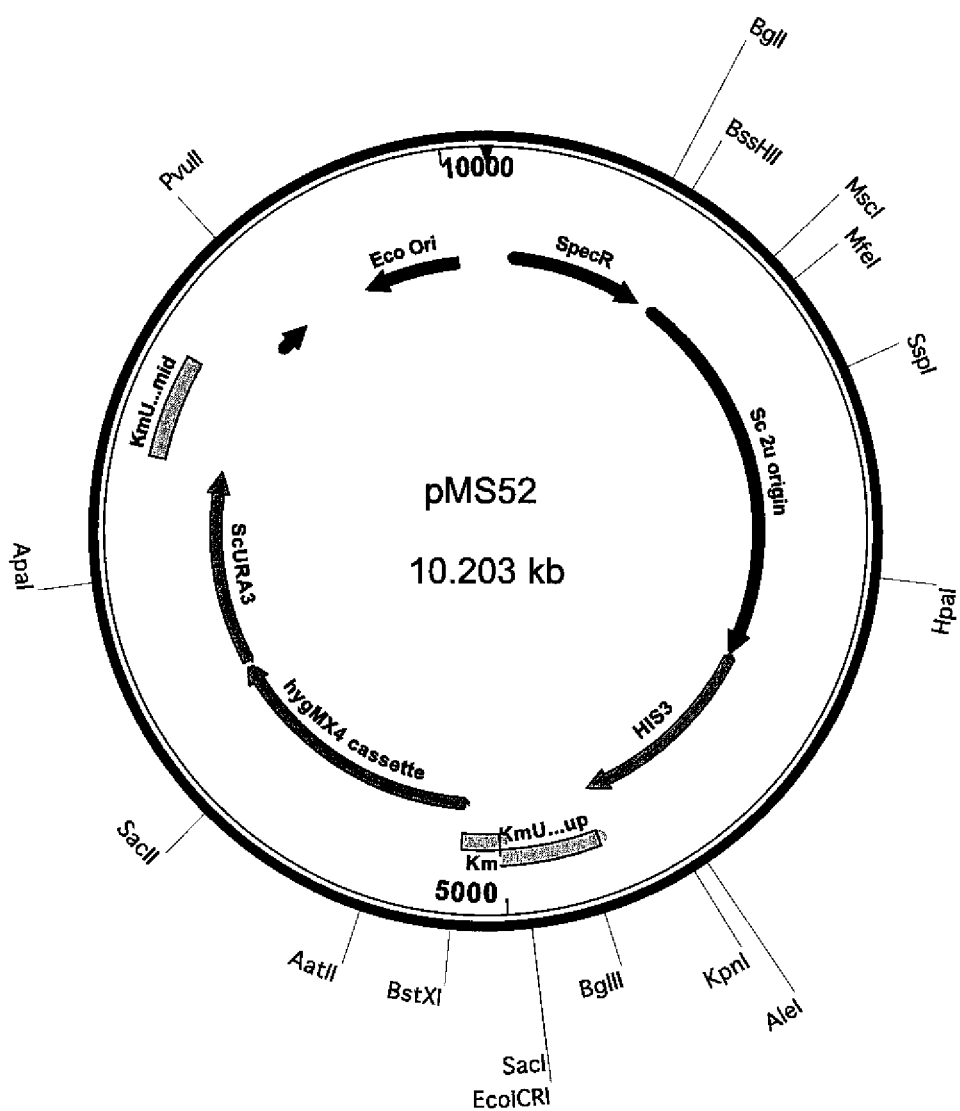
FIG. 1. Structure of the plasmid pMS52 containing the cassette used to delete the KmURA3 gene from the *K. marxianus* strain SD98.
Figure 2:
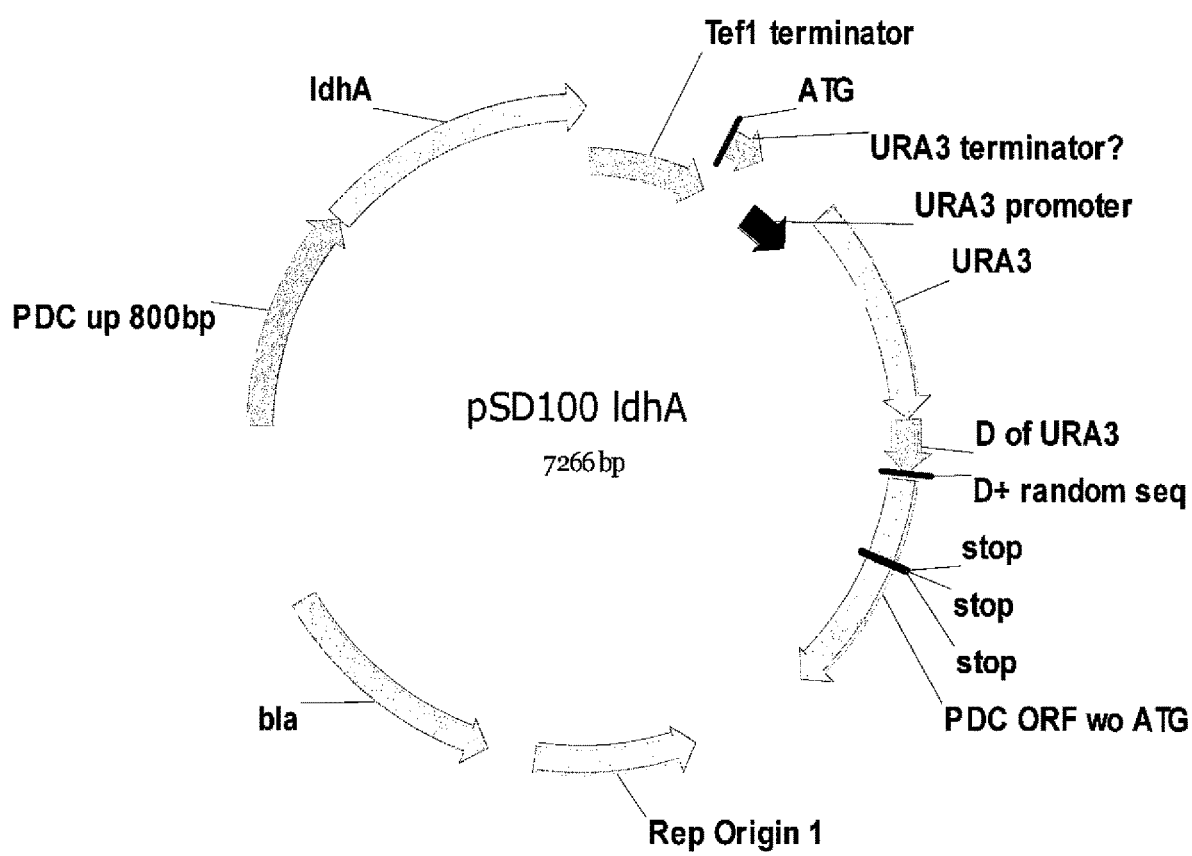
FIG. 2. Structure of the plasmid pSD100 ldhA containing the cassette used to install the ldhA gene cassette at the PDC1 locus in the *K. marxianus* strain SD98.
Figure 3:
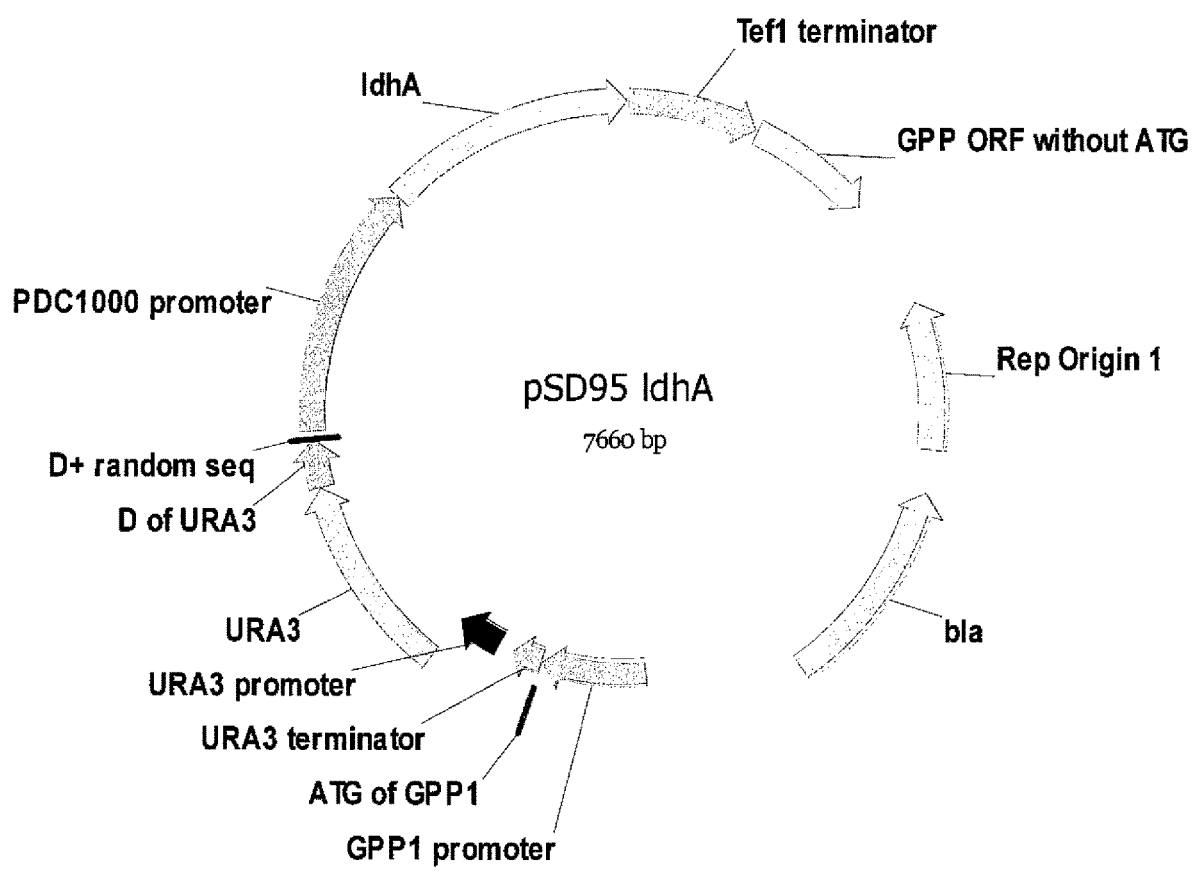
FIG. 3. Structure the plasmid pSD95 ldhA containing the cassette used to install the ldhA gene cassette at the GPP1 locus in the *K. marxianus* strain SD98.
Figure 4:
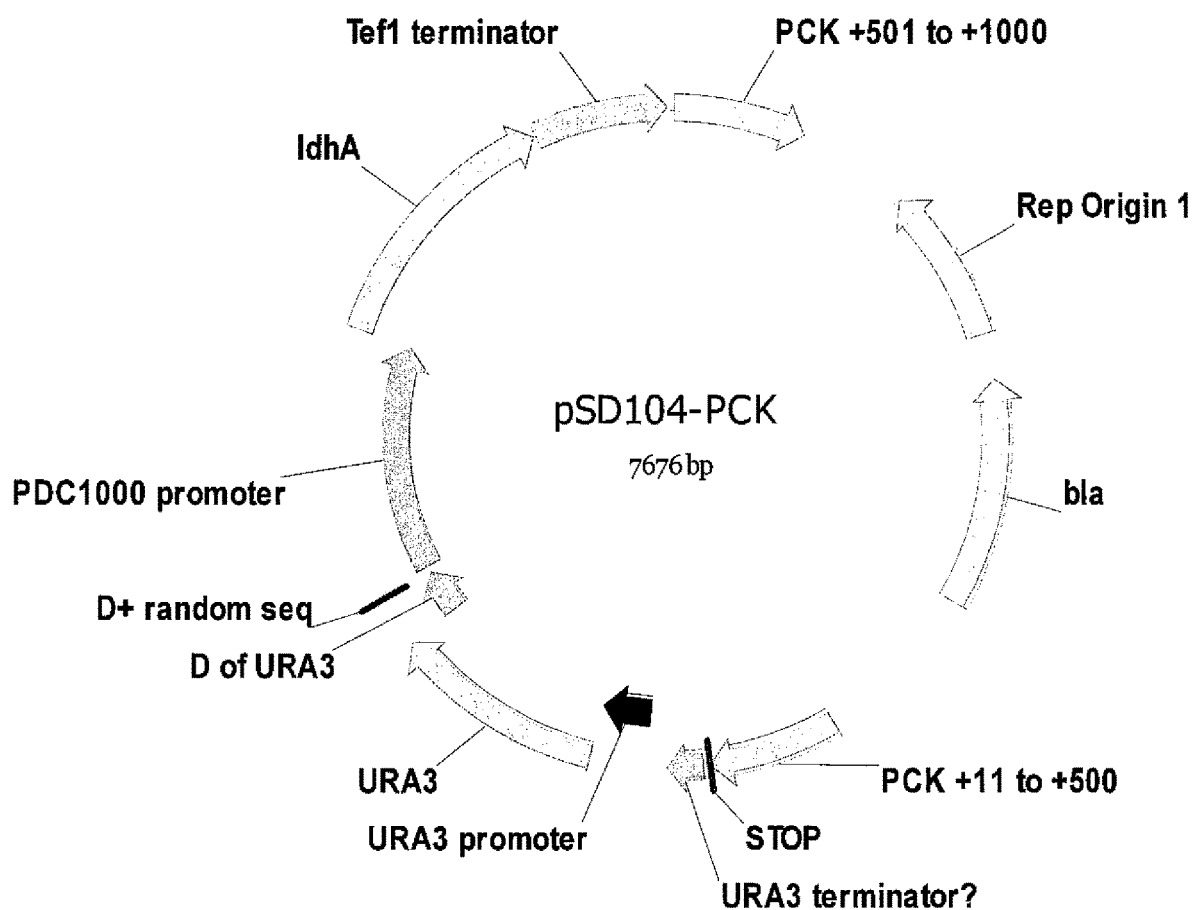
FIG. 4. Structure the plasmid pSD104-PCK1 containing the cassette used to install the ldhA gene cassette at the PCK1 locus in the *K. marxianus* strain SD98.
Figure 5:
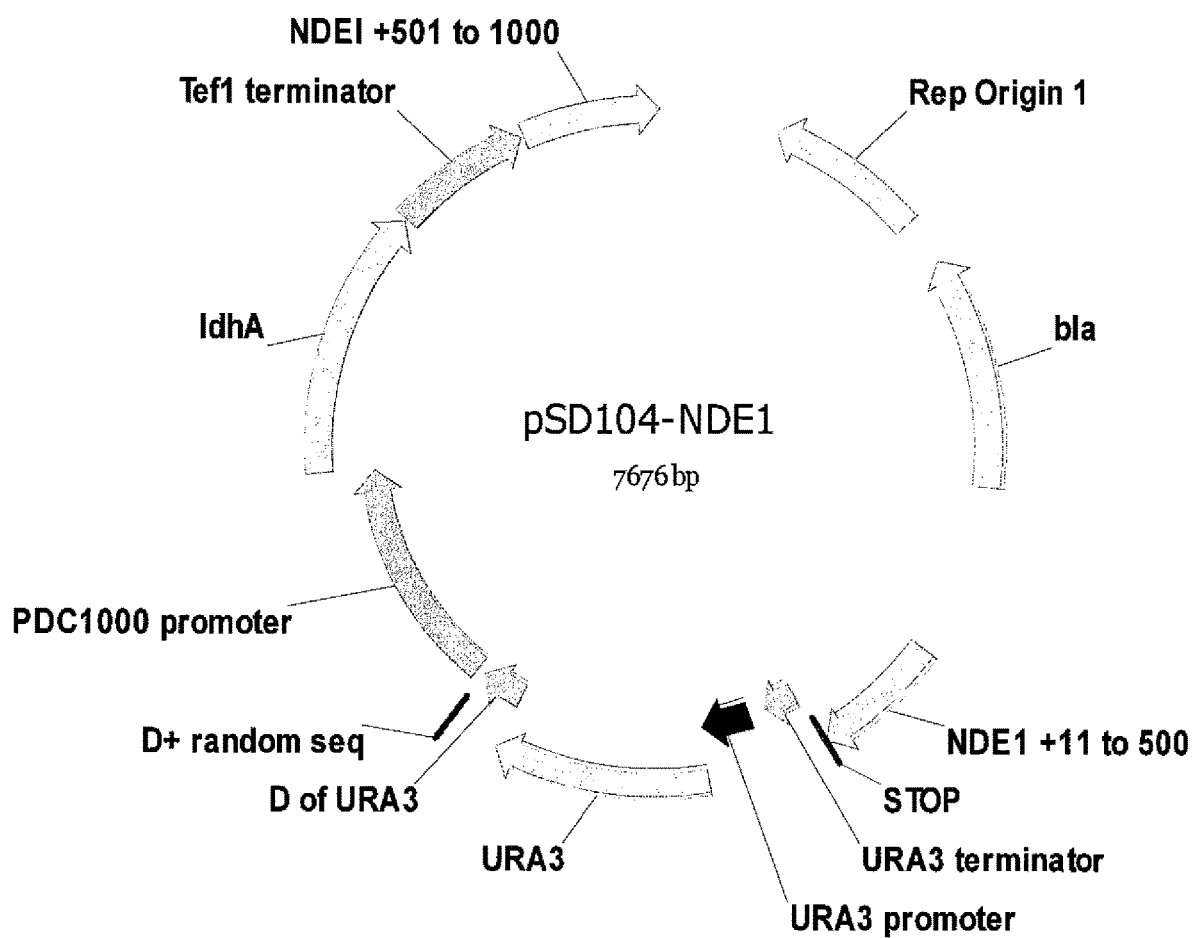
FIG. 5. Structure the plasmid pSD104-NDE1 containing the cassette used to install the ldhA gene cassette at the NDE1 locus in the *K. marxianus* strain SD98.
Figure 6:
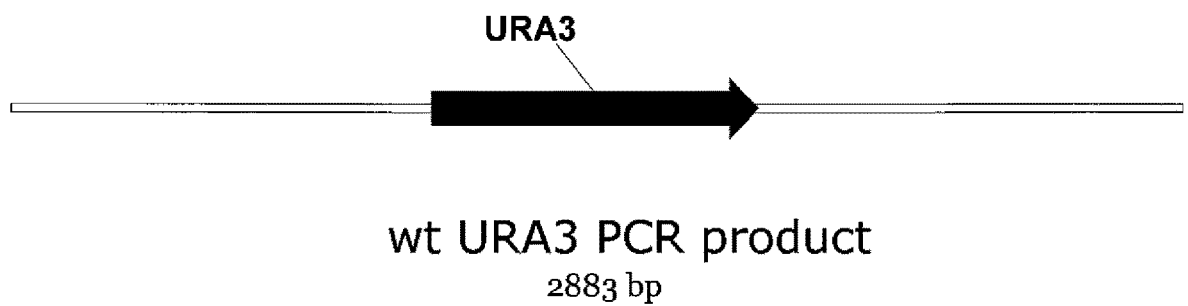
FIG. 6. Structure the plasmid PCR product containing the wild type KmURA3 gene and 1033 bp upstream flanking sequence and 1046 bp downstream flanking sequence of the URA3 gene, of *K. marxianus* strain SD98, used to reinstall the KmURA3 gene at the delta-KmURA3 locus in the *K. marxianus* strain.

Various non-limiting embodiments of the disclosure will now be described herein and illustrated in the accompanying drawings. A person having ordinary skill in the art will understand that the features, structures, components, or characteristics described or illustrated in connection with one non-limiting embodiment may be combined with the features, structures, components, or characteristics of one or more other non-limiting embodiments. Such combinations are intended to be included within the scope of the disclosure. A person having ordinary skill in the art will also understand that that the features, structures, components, or characteristics described or illustrated in connection with one or more non-limiting embodiments can be modified or varied without departing from the scope and spirit of the invention.

To facilitate understanding of the invention, a description of nomenclature is provided below.

In regards to nomenclature, a bacterial gene or coding region is usually named with lower case letters in italics, for example "ldhA" from *E. coli*, while the enzyme or protein encoded by the gene can be named with the same letters, but with the first letter in upper case and without italics, for example "LdhA". A yeast gene or coding region is usually named with upper case letters in italics, for example "PDC1", while the enzyme or protein encoded by the gene can be named with the same letters, but with the first letter in upper case and without italics, for example "Pdc1" or "Pdc1p", the latter of which is an example of a convention used in yeast for designating an enzyme or protein. The "p" is an abbreviation for protein, encoded by the designated gene. The enzyme or protein can also be referred to by a more descriptive name, for example, D-lactate dehydrogenase (ldhA/LdhA) or pyruvate decarboxylase (PDC1/Pdc1), referring respectively to the two above examples. A gene or coding region that encodes one example of an enzyme that has a particular catalytic activity can have several different names because of historically different origins, functionally redundant genes, genes regulated differently, or because the genes come from different species. For example a gene that encodes glycerol-3-phosphate dehydrogenase can be named GPD1, GDP2, or DAR1, as well as other names. To specify the organism from which a particular gene was derived, the gene name can be preceded by two letters indicating the genus and species. For example, the KURA3 gene is derived from *Kluyveromyces marxianus* and the ScURA3 gene is derived from *Saccharomyces cerevisiae*.

Note that all isomers of lactic acid and any lactic acid analog can exist in solid, liquid, or solution form as a protonated acid (also known as a free acid) or as an ionized salt. In aqueous solution, both protonated and ionic forms co-exist in an equilibrium. Since it would be cumbersome to refer to all forms of such compounds, any mention of either the acid form or the salt form (for example D-lactic acid (D-LAC) or beta-chlorolactate) includes all forms or mixtures of all forms.

To facilitate understanding of the invention, a number of terms are defined below, and others are found elsewhere in the specification.

"Yeast" means any fungal organism that is capable of growing in a single cell state under some conditions. Some yeast strains can also grow in a hyphal state or psuedohyphal (i.e., short hyphae) state under some conditions, such as under starvation. In particular, yeast includes, but is not limited to, organisms in the genera *Saccharomyces, Kluyveromyces, Issatchenkia, Pichia, Hansenula, Candida, Yarrowia, Zygosaccharomyces, Schizosaccharomyces*, and *Lachancea*.

"Cassette" or "expression cassette" means a deoxyribose nucleic acid (DNA) sequence that is capable of encoding and producing, or alternatively eliminating or reducing, one or more desired proteins or enzymes when installed in a host organism. A cassette for producing a protein or enzyme typically comprises at least one promoter, at least one coding sequence, and optionally at least one terminator. If a gene to be expressed is heterologous or exogenous, the promoter and terminator are usually derived from two different genes or from a heterologous gene, in order to prevent double recombination with the native gene from which the promoter or terminator was derived. A cassette can optionally and preferably contain one or two flanking sequence(s) on either or both ends that is/are homologous to a DNA sequence in a host organism, such that the cassette can undergo homologous recombination with the host organism, either with a chromosome or a plasmid, resulting in integration of the cassette into said chromosome or plasmid. If only one end contains a flanking homology, then the cassette in a circular format can integrate by single recombination at the flanking sequence. If both ends of a cassette contain flanking homologies, then the cassette in a linear or circular format can integrate by double recombination with the surrounding flanks. A cassette can be constructed by genetic engineering, where for example a coding sequence is expressed from a non-native promoter, or it can use the naturally associated promoter. A cassette can be built into a plasmid, which can be circular, or it can be a linear DNA created by polymerase chain reaction (PCR), primer extension PCR, or by in vivo or in vitro homologous recombination. A cassette can be designed to include a selectable marker gene or DNA sequence that upon integration is surrounded by a direct repeat sequence of about 30 base pairs or more (the same sequence, in the same orientation present both ends of the integrated selectable gene), such that the selectable marker can be deleted by homologous recombination between the direct repeats after the cassette is integrated into a chromosome or plasmid. Useful selectable marker genes include, but are not limited to, antibiotic G418 resistance (kan or kanR), hygromycin resistance (hyg or hygR), zeocin resistance (zeo or zeoR), naturicin resistance (nat or natR), URA3, TRP1, TRP5, LEU2, and HIS3. For the biosynthetic genes to be used as a selectable marker, the host strain must, of course, contain a mutation in the corresponding gene, preferably a null mutation. For the antibiotic resistance genes, the resistance gene usually requires a promoter that functions well enough in the host yeast strain to enable selection. Although a gene that is desired to be expressed can be installed in a host strain in the form of a cassette, a gene, for example a coding sequence from start codon to stop codon can be integrated into a host chromosome or plasmid without a promoter or terminator such that the incoming coding sequence precisely or approximately replaces the coding sequence of a gene native to the host strain, such that after integration, the incoming coding region is expressed from the remaining promoter of the host coding sequence that was replaced by the incoming coding sequence.

"D-lactate dehydrogenase" means any enzyme that catalyzes the formation of D-lactate from pyruvate. "L-lactate dehydrogenase" means any enzyme that catalyzes the formation of L-lactate from pyruvate. The necessary reducing equivalent for either of these reactions can be supplied by NADH, NADPH, or any other reducing equivalent donor.

"Gibson method" means a method for joining together two or more linear DNA fragments that have short (about 15-40 base pairs) overlapping homology at their ends. This method can be used to construct plasmids from synthetic linear DNA fragments, PCR fragments, or fragments generated by restriction enzymes. Kits can be purchased to perform the Gibson method, for example the NEBuilder® kit (New England BioLabs, Ipswitch, Mass., USA), and used as instructed by the manufacturer.

"Transformant" means a cell or strain that results from installation of a desired DNA sequence, either linear or circular, and either autonomously replicating or not, into a host or parent strain.

"Titer" means the concentration of a compound in a fermentation broth, usually expressed as grams per liter (g/L) or as % weight per volume (%). Titer is determined by any suitable analytical method, such as quantitative analytical chromatography, for example high pressure liquid chromatography (HPLC) or gas chromatography (GC), with a standard curve made from external standards, and optionally with internal standards.

"Yield" means the grams of product per gram of carbon source used during fermentation. This is typically calculated based on titer, final liquid volume, and amount of carbon source supplied, with the final volume corrected for volumes sampled, fed, and/or evaporated. It is usually expressed as grams per gram (g/g) or as a % weight per weight (%).

"Time" means the time elapsed from inoculation to sampling or harvesting in a fermentation, typically measured in hours.

"Specific productivity" means the rate of product formation in grams of product produced in given volume of fermentation broth in a given period of time, typically expressed in grams per liter-hours (g/L-hr). The "average specific productivity" means the specific productivity where the period of time is the entire fermentation from inoculation to sampling or harvest. The average specific productivity is lower than the specific productivity from the middle of a fermentation, since specific productivity is lower than average during the early growth period and during the later stages. Average specific productivity can be calculated by dividing final titer by the number of hours at harvest. Note that some published specific productivities are clearly not average specific productivities, although the period of measurement is not explicitly given (see Table 1 for some examples).

"pKa" means the pH at which an acid in solution is half in the conjugate base state, which is typically an ionic or salt form. The pKa for L-LAC and D-LAC is published to be from 3.78 to 3.86, although the exact pKa can vary slightly with temperature, concentration, and concentration of other solutes. For lactic acid, the conjugate base state is the lactate ion, so the pKa is the pH where the concentration of the lactate ion equals the concentration of the protonated or "free acid" state. The pKa can be measured by the well-known method of performing an acid-base titration and taking the midpoint of the titration curve. One skilled in the art will know that in aqueous solution, D-lactic acid exists to some extent in two forms, the protonated acid form and the ionized salt (i.e., conjugate base) form. As such, depending on context, the terms "D-lactate", "D-lactic acid", and "D-LAC" can mean either form, or a mixture of the two forms. In particular, when discussing titers and yields, the sum of both forms is meant to be included, but it is expressed in terms of the free acid, in other words, titer and yield is expressed as if any salt form that is present is converted to the free acid form.

"Heterologous" means a gene or protein that is not naturally or natively found in an organism, but which can be introduced into an organism by genetic engineering, such as by transformation, mating, or transduction. A heterologous gene can be integrated (i.e., inserted or installed) into a chromosome, or contained on a plasmid. The term "exogenous" means a gene or protein that has been introduced into, or altered, in an organism for the purpose of increasing, decreasing, or eliminating an activity, by genetic engineering, such as by transformation, mating, transduction, or mutagenesis. An exogenous gene or protein can be heterologous, or it can be a gene or protein that is native to the host organism, but altered by one or more methods, for example, mutation, deletion, change of promoter, change of terminator, duplication, or insertion of one or more additional copies in the chromosome or in a plasmid. Thus, for example, if a second copy of a DNA sequence is inserted at a site in the chromosome that is distinct from the native site, the second copy would be exogenous.

"Plasmid" means a circular or linear DNA molecule that is substantially smaller than a chromosome, is separate from the chromosome or chromosomes of a microorganism, and replicates separately from the chromosome or chromosomes. A plasmid can be present in about one copy per cell or in more than one copy per cell. Maintenance of a plasmid within a microbial cell usually requires growth in a medium that selects for presence of the plasmid, for example using an antibiotic resistance gene, or complementation of a chromosomal auxotrophy. However, some plasmids require no selective pressure for stable maintenance, for example the 2 micron circle plasmid in many *Saccharomyces* strains.

"Chromosome" or "chromosomal DNA" means a linear or circular DNA molecule that is substantially larger than a plasmid and usually does not require any antibiotic or nutritional selection. In the invention, a yeast artificial chromosome (YAC) can be used as a vector for installing heterologous and/or exogenous genes, but it would require selective pressure for maintenance.

"Overexpression" means causing the enzyme or protein encoded by a gene or coding region to be produced in a host microorganism at a level that is higher than the level found in the wild type version of the host microorganism under the same or similar growth conditions. This can be accomplished by, for example, one or more of the following methods: installing a stronger promoter, installing a stronger ribosome binding site, installing a terminator or a stronger terminator, improving the choice of codons at one or more sites in the coding region, improving the mRNA stability, or increasing the copy number of the gene either by introducing multiple copies in the chromosome or placing the cassette on a multi-copy plasmid. An enzyme or protein produced from a gene that is overexpressed is said to be "overproduced." A gene that is being overexpressed or a protein that is being overproduced can be one that is native to a host microorganism, or it can be one that has been transplanted by genetic engineering methods from a different organism into a host microorganism, in which case the enzyme or protein and the gene or coding region that encodes the enzyme or protein is called "foreign" or "heterologous." Foreign or heterologous genes and proteins are by definition overexpressed and overproduced, since they are not present in the native, wild type, parent or precursor host organism.

"Homolog" means a gene, DNA sequence, or protein that performs a similar biological function to that of another gene, DNA sequence, or protein, and that has at least 25% sequence identity (when comparing protein sequences or comparing the protein sequence derived from gene sequences) with said another gene, DNA sequence, or protein, as determined by the Basic Local Alignment Search Tool (BLAST) computer program for sequence comparison (Altschul et al, 1990; Altschul et al, 1997) and allowing for deletions and insertions. An example of a homolog of the *K. marxianus* PDC1 gene would be the PDC1 gene from *S. cerevisiae*.

"Analog" means a gene, DNA sequence, or protein that performs a similar biological function to that of another gene, DNA sequence, or protein, but where there is less than 25% sequence identity (when comparing protein sequences or comparing the protein sequence derived from gene sequences) with said another gene, DNA sequence, or protein, as determined by the BLAST computer program for sequence comparison (Altschul et al, 1990; Altschul et al, 1997), and allowing for deletions and insertions. An example of an analog of the *K. marxianus* Gpd1 protein would be the *K. marxianus* Gut2 protein, since both proteins are enzymes that catalyze the same reaction, but there is no significant sequence homology between the two enzymes or their respective genes. A person having ordinary skill in the art will know that many enzymes and proteins that have a particular biological function (in the immediately above example, glycerol-3-phosphate dehydrogenase), can be found in many different organisms, either as homologs or analogs, and since members of such families of enzymes or proteins share the same function, although they may be slightly or substantially different in structure. Different members of the same family can in many cases be used to perform the same biological function using current methods of genetic engineering. Thus, for example, a gene that encodes D-lactate dehydrogenase could be obtained from any of many different organisms.

"Mutation" means any change from a native or parent DNA sequence, for example, an inversion, a duplication, an insertion of one or more base pairs, a deletion of one or more base pairs, a point mutation leading to a base change that creates a premature stop codon, or a missense mutation that changes the amino acid encoded at that position. "Null mutation" means a mutation that effectively eliminates the function of a gene. A complete deletion of a coding region would be a null mutation, but single base changes can also result in a null mutation. "Mutant", "mutated strain", "mutated yeast strain", or a strain "that has been mutated" means a strain that comprises one or more mutations when compared to a native, wild type, parent or precursor strain.

The phrase "a mutation that eliminates or reduces the function of" means any mutation that lowers any assayable parameter or output, of a gene, protein, or enzyme, such as mRNA level, protein concentration, or specific enzyme activity of a strain, when said assayable parameter or output is measured and compared to that of the unmutated parent strain. Such a mutation is preferably a deletion mutation, but it can be any type of mutation that accomplishes a desired elimination or reduction of function.

"Strong constitutive promoter" means a DNA sequence that typically lies upstream (to the 5' side of a gene when depicted in the conventional 5' to 3' orientation), of a DNA sequence or a gene that is transcribed by an RNA polymerase, and that causes said DNA sequence or gene to be expressed by transcription by an RNA polymerase at a level that is easily detected directly or indirectly by any appropriate assay procedure. Examples of appropriate assay procedures include quantitative reverse transcriptase plus PCR, enzyme assay of an encoded enzyme, Coomassie Blue-stained protein gel, or measurable production of a metabolite that is produced indirectly as a result of said transcription, and such measurable transcription occurring regardless of the presence or absence of a protein that specifically regulates the level of transcription, a metabolite, or an inducer chemical. By using well-known methods, a strong constitutive promoter can be used to replace a native promoter (a promoter that is otherwise, naturally existing upstream from a DNA sequence or gene), resulting in an expression cassette that can be placed either in a plasmid or chromosome and that provides a level of expression of a desired DNA sequence or gene at a level that is higher than the level from the native promoter. A strong constitutive promoter can be specific for a species or genus, but often a strong constitutive promoter from a yeast can function well in a distantly related yeast. For example, the TEF1 (translation elongation factor 1) promoter from *Ashbya gossypii* functions well in many other yeast genera, including *K. marxianus*.

"Microaerobic" or "microarobic fermentation conditions" means that the supply of air to a fermentor is less than 0.1 volume of air per volume of liquid broth per minute (vvm).

"Chemically defined medium", "minimal medium", or "mineral medium" means any fermentation medium that is comprised of purified chemicals such as mineral salts (for example sodium, potassium, ammonium, magnesium, calcium, phosphate, sulfate, chloride, etc.) which provide necessary element such as nitrogen, sulfur, magnesium, phosphorus (and sometimes calcium and chloride), vitamins (when necessary or stimulatory for the microbe to grow), one or more pure carbon sources, such as a pure sugar, glycerol, ethanol, etc., trace metals as necessary or stimulatory for the microbe to grow (such as iron, manganese, copper, zinc, molybdenum, nickel, boron and cobalt), and optionally an osmotic protectant such as glycine betaine, also known as betaine. Except for the optional osmoprotectant and vitamin(s), such media do not contain significant amounts of any nutrient or mix of more than one nutrient that is not essential for the growth of the microbe being fermented. Such media do not contain any significant amount of rich or complex nutrient mixtures such as yeast extract, peptone, protein hydrolysate, molasses, broth, plant extract, animal extract, microbe extract, whey, Jerusalem artichoke powder, and the like. For producing a commodity chemical by fermentation where purification of the desired chemical by simple distillation is a not an economically attractive option, a minimal medium is preferred over a rich medium because a minimal medium is usually less expensive, and the fermentation broth at the end of fermentation usually contains lower concentrations of unwanted contaminating chemicals that need to be purified away from the desired chemical.

"Fermentation production medium" means the medium used in the last tank, vessel, or fermentor, in a series comprising one or more tanks, vessels, or fermentors, in a process wherein a microbe is grown to produce a desired product (for example D-LAC or L-LAC). For production of a commodity chemical by fermentation such as D-LAC or L-LAC, where extensive purification is necessary or desired, a fermentation production medium that is a minimal medium is preferred over a rich medium because a minimal medium is often less expensive, and the fermentation broth at the end of fermentation usually contains lower concentrations of unwanted contaminating chemicals that need to be purified away from the desired chemical. Although it is generally preferred to minimize the concentration of rich nutrients in such a fermentation, in some cases it is advantageous for the overall process to grow an inoculum culture in a medium that is different from the fermentation production medium, for example to grow a relatively small volume (usually 10% or less of the fermentation production medium volume) of inoculum culture grown in a medium that contains one or more rich ingredients. If the inoculum culture is small relative to the production culture, the rich components of the inoculum culture can be diluted into the fermentation production medium to the point where they do not substantially interfere with purification of the desired product. A fermentation production medium must contain a carbon source, which is typically a sugar, glycerol, fat, fatty acid, carbon dioxide, methane, alcohol, or organic acid. In some geographic locations, for example in the Midwestern United States, D-glucose (dextrose) is relatively inexpensive and therefore is useful as a carbon source. Most prior art publications on lactic acid production by a yeast use dextrose as the carbon source. However, in some geographic locations, such as Brazil and much of Southeast Asia, sucrose is less expensive than dextrose, so sucrose is a preferred carbon source in those regions.

"Final pH" means the pH of a fermentation broth at the end of a fermentation when the fermentation is considered complete, fermentation is stopped, and the broth is harvested. Although it is preferred that the final pH of a lactic acid fermentation be below the pKa of lactic acid, it is also preferred that the pH during fermentation be controlled by addition of a "base" (an alkaline substance), to prevent the pH from falling too quickly or ending too low. The "base" can be in a solution, suspension, slurry, or solid form. The "base" can be a hydroxide, oxide, carbonate, or bicarbonate salt of sodium, ammonium, potassium, magnesium, or calcium. For production of lactic acid, a preferred base is a slurry of calcium hydroxide or powdered calcium hydroxide, which leads to the formation of some calcium lactate mixed with the protonated acid form in the fermentation broth. The resulting fermentation broth at the end of fermentation can be treated with sulfuric acid, which causes precipitation of calcium sulfate (gypsum), which aids in the removal of calcium, to increase the proportion of the lactic acid that is present in the protonated form. The feeding of the base to control pH can be done manually or by an automatically controlled pump or auger, as called for by pH measurements, which can be obtained manually or by continuous monitoring through a pH probe immersed in the fermentation vessel.

To facilitate understanding of the invention, various genes are listed in Table 2 below. The sequence information for plasmid and exogenous genes used in the present invention are listed in the Table 3 below.

The prior art (described above) discloses several genetically engineered yeasts that produce D-LAC, but as mentioned above, none of the published parameters come close to those necessary for an economically attractive process. Furthermore, D-LAC is generally more toxic than L-LAC to organisms, so techniques and approaches for developing strains and processes for producing L-LAC cannot be assumed to be directly applicable to techniques and approaches for producing D-LAC.

*K. marxianus* strains were grown at 37° C. and stored at −80° C. in 20 to 40% glycerol. Transformation of *K. marxianus* was done by the "Transformation protocol for gene targeting" method of Abdel-Banat et al (2010) with the modification that the growth medium for making transformation-competent cells was altered to prevent the cultures from becoming too acidic. The growth medium for making competent cells contained, per liter, 10 g yeast extract, 20 peptone, 3 g glucose, and 20 g glycerol.

DNA cassettes were constructed in plasmids in *E. coli* DH 5-alpha strain (New England BioLabs, Ipswitch, Mass., USA) using standard DNA manipulation methods well known to those skilled in the art, including synthetic "g-block" DNA sequences (Integrated DNA Technologies, Woodland, Tex., USA), high fidelity PCR, restriction enzymes, DNA ligase, and the Gibson method using the NEBuilder kit (New England BioLabs, Ipswitch, Mass., USA).

The general design of cassettes for integration have the following features, in the following order: (1) upstream homology to target locus, (2) strong constitutive promoter, (3) coding region to be expressed, (4) terminator, (5) homology to downstream of target locus, (6) selectable (and optionally counter-selectable) marker gene, and (7) homology to a middle sequence of target locus. Selection for the marker gene causes integration between the upstream homology and middle homology of the target locus. Transformants containing the correct integration are identified by diagnostic PCR that shows both an upstream and a downstream junction fragment of the correct expected size. Counter selection, for example against a URA3 gene, leads to looping out of the selectable and counter-selectable marker URA3 gene and the middle homology sequence by recombination of the downstream homology component in the cassette with the same chromosomal sequence that occurs just downstream of the integrated cassette. If the target locus is intended to be deleted without a concomitant insertion, then the "(2) strong constitutive promoter, (3) coding region to be expressed, (4) terminator" portion of the general design described above is omitted.

EXAMPLES

The following examples are provided to further explain the invention but are not intended to limit the scope of the invention.

Example 1

Construction of Strain SD1555

The starting strain was *K. marxianus* SD98, a wild Crabtree positive strain isolated from rotting bagasse explained in the US Patent Application Publication No. 2015/0240270. The native KmURA3 gene was deleted from SD98 to give strain KMS95 in order to use a URA3 gene as a selectable marker for integrative transformation. The KmURA3 gene was deleted by integrating a cassette constructed on plasmid pMS52 (SEQ ID No. 1). The cassette was obtained from the plasmid as a linear fragment, and integrated into SD98, selecting for hygromycin resistance (300 mg/L hygromycin B in YPD medium after a 3-hour grow out period in YPD without hygromycin before plating on hygromycin plates). The hygromycin resistance gene was driven by the *Ashbya gossypii* TEF1 promoter. After correct integration of the cassette at the KmURA3 locus, a portion of the interrupted KmURA3 gene and the hygromycin resistance gene were flanked by direct repeats to allows the sequences between the direct repeats to be looped out by homologous recombination with a second selection for resistance to 5-fluoro-orotic acid (5-FOA), which counter-selects the URA3 gene; in other words, it selects for loss of the URA3 gene. Selection for 5-FOA resistance was done by plating about 100 million cells on CM glucose minus uracil medium (Teknova, Hollister, Calif., USA) supplemented with 1 g/L 5-FOA and 24 mg/L uracil.

Four different cassettes designed to express the *E. coli* ldhA gene were constructed on plasmids. In all four cases, the ldhA gene was expressed from the *K. marxianus* PDC1 promoter. The four different cassettes were designed to insert into four different loci in KMS95: the PDC1 (pyruvate decarboxylase) locus (SEQ ID No. 2), the GPP1 (glycerol-3-phosphate phosphatase) locus (SEQ ID No. 3), the PCK1 (phosphoenol pyruvate carboxykinase) locus (SEQ ID No. 4), and the NDE1 (NADH dehydrogenase 1) locus (SEQ ID No. 5). The cassettes were designed to integrate at the target loci by homologous recombination, selecting for the *S. cerevisiae* URA3 gene on CM glucose minus uracil medium (Teknova, Hollister, Calif., USA), and then in a second step for the URA3 gene to be looped out by homologous recombination between direct repeats of a downstream flank, selecting for resistance to 5-FOA, as described above, in order to reuse the URA3 gene for subsequent transformations. At each transformation step and each loopout step, single colonies were restreaked one or more times as necessary to free the correct strain from background cells, and to eliminate heterozygous diploids. Correct insertions and correct loop-outs were identified by PCR using appropriate primers that bracketed the borders between the ends of the cassettes and the chromosomal sequences at the target locus that are just upstream or just downstream of the integrated cassette. PCR diagnostics could not distinguish correctly integrated cassettes in haploids from correctly integrated homozygous diploids; so this distinction was not made at any step of the constructions. Starting with strain KMS95, the four ldhA cassettes were installed, one at a time in the order listed above. After each initial integration of a cassette, the URA3 gene was looped out by the 5-FOA counterselection. After the fourth cassette was thus installed, the native KmURA3 gene (SEQ ID No. 6) was re-installed by transfounation of a linear DNA fragment obtained by PCR from SD98 chromosomal DNA as a template to give a uracil prototroph by selection on CM glucose minus uracil plates. The resulting strain, which now contains four copies of the integrated ldhA gene, was named SD1555. Insertion of the cassette into the PDC1 gene blocks the unwanted synthesis of ethanol. Insertion of the cassette into the GPP1 gene blocks the unwanted synthesis of glycerol. Insertion of the cassette into the PCK1 gene blocks the unwanted growth of the yeast on D-LAC or L-LAC as a carbon source, because strains that have reduced or eliminated Pck1 activity cannot perform glucogenesis, and gluconeogenesis is necessary for growth on non-fermenatble carbon sources such as D-LAC or L-LAC. Inability to grow on D-LAC or L-LAC is a desirable trait, because it prevents a loss of titer at the end of fermentation when the concentration of sugar is low or zero. Although a pck1 mutation is preferable, because PCK1 encodes the first committed step in the gluconeogenic pathway, any other mutation that reduces or eliminates gluconeogenesis, for a example a mutation that reduces or eliminates fructose 1,6-bisphosphate phosphatase activity, could also lead to a similar desirable result, namely reduced or eliminated gluconeogenesis. Insertion of the cassette into the NDE1 gene causes conservation of cytoplasmic NADH, one of the substrates for biosynthesis of D-LAC.

Example 2

Construction of Strain SD1566

Derivatives of SD1555 that were resistant to beta-chlorolactate (MilliporeSigma, St. Louis, Mo., USA) were selected as follows. A lawn of about $10^8$ cells of SD1555 was spread evenly on a plate containing SDM2 medium containing 20 g/L glucose. A small spec of beta-chlorolactate was placed at the center of the plate. The beta-chlorolactate was not specified as to isomer, so it was assumed to be a racemic mixture of D- and L-isomers. After three days, a lawn grew around a central killing zone. At the edge of the killing zone, several individual colonies appeared. Several such colonies were restreaked to plates containing SDM2 with 20 g/L glucose and 0.75 g/L beta-chlorolactate. After three days at 37° C., the colonies resistant to beta-chlorolactate were visible. The parent strain SD1555 did not give visible single colonies on the same plate at three days.

In addition to beta-chlorolactate, there are many other lactic acid analogs that can be used to select for resistant mutants that have desirable properties. Examples of lactic acid analogs include, but are not limited to 3-chlorolactate (beta-chlorolactate), 3-dichlorolactic acid, 3-trichorolactic acid, 3-fluorolactic acid, 3-difluorolactic acid, 3-trifluorolactic acid, 3-bromolactic acid, 3-dibromolactic acid, 3-tribromolactic acid, all possible 2-halo-substituted derivatives of lactic acid, all chiral forms of any of the above analogs, or any salt of any of the above. "Lactic acid analog" means any compound that is structurally related to lactic acid and inhibits growth of a parent yeast strain under appropriate conditions, and includes the set of compounds disclosed above. Note that the term "analog" in the context of "lactic acid analog" has a meaning different from that when used in the context of a gene or protein sequence. As mentioned above, in the context of a gene or protein, the term "analog" refers to a positively functioning alternative, while in the context of "lactic acid analog", the word means an interfering, toxic compound.

A yeast strain genetically engineered to produce lactic acid that has been "mutated to confer resistance to a lactic acid analog at a higher concentration when compared to an isogenic strain that has not been mutated" means a strain that contains one or more mutations relative to a parent strain, for which a concentration of a lactic acid analog in liquid or agar containing medium can be found, where said mutated strain gives visibly better growth or larger colonies than the parent strain when the two strains are grown in similar parallel liquid cultures or streaked beside each other on the same Petri plate, after incubation for between about one and five days at a temperature that is appropriate for visible growth of the mutated strain. In the example given above, a beta-chlorolactate concentration of 0.75 g/L and incubation for three days at 37° C. was determined to show good contrast in colony size on agar plates, but for other yeast strains and species, other conditions might show better contrast between parents and mutants. Appropriate conditions for establishing resistance to a lactic acid analog in a strain by differentiating said resistant strain from a parent strain can be determined by routine experimentation, by plating or growing a parent strain and a mutant strain in media containing a range of concentrations of said lactic acid analog from 0 g/L to about 10 g/L.

For example, by systematically varying the concentration of a lactic acid analog in petri plates containing a minimal medium that supports growth of the parent strain, incubating at a temperature where the parent strain is known to grow well, and checking the plates on a daily basis to score the plates when a contrast in colony size between mutant and parent is visible, strains that are resistant to a lactic acid analog when compared to a parent strain can be identified. Alternatively, relative resistance to a lactic acid analog can be determined by obtaining growth curves of mutant and parent strains in liquid media that contain a range of lactic acid analog concentrations from 0 to 10 g/L.

"Parent strain" means a starting strain that can be subjected to one or more conditions that leads to a new derivative or descendant strain that comprises a genetic change that ultimately leads to at least one change in a measurable property of the new derivative strain that is significantly different from that property of the parent strain, for example lactic acid titer, lactic acid yield, specific productivity of lactic acid, or titer of any measurable byproduct, such as pyruvic acid. Said "one or more conditions" can be any one or more of a number of manipulations performed on the parent strain, for example genetic engineering involving installation of DNA that alters the genetic makeup of the strain, selection of spontaneous mutants as described above for beta-chlorolactate resistance, and applying any of a number of well-known mutagenesis procedures to a parent strain before subjecting a mutagenized population of cells to a selection or screen for a desired property, for example for resistance to a lactic acid analog. Well known mutagenesis procedures include exposing cells to a chemical mutagen, for example nitrosoguanidine (also known as NTG, MNNG, and N-methyl-N'-nitro-N-nitrosoguanidine), ethylmethanesulfonate (also known as EMS), or mutagenic radiation, for example X-rays or ultraviolet light. An appropriate dose of mutagen can be determined for a parent strain by exposing a population of live parent cells to a range of mutagen doses, and choosing a dose and conditions that leave a live subpopulation that is sufficiently large that it contains desired mutants of the desired type, for example beta-chlorolactate resistant mutants. In the art, typical mutagen doses are chosen that kill about 10% to 95% of the parent population. Strains resistant to beta-chlorolactate or other lactic acid analog can be selected from a parent strain that has already been genetically engineered to produce lactic acid, but strains resistant to a lactic acid analog can also be selected from parent strains that have not been engineered for lactic acid production. In this latter case, resistant mutants can be engineered for lactic acid production and then screened for improved lactic acid production compared to strains similarly engineered from parent strains that have not been selected for resistance to a lactic acid analog.

Figure 7:
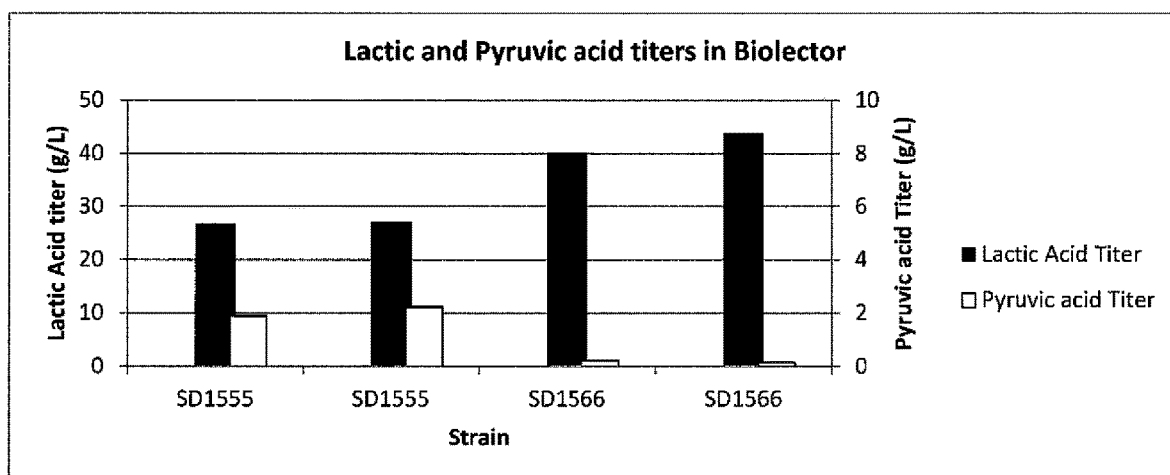
FIG. 7. Production of D-lactate and pyruvate by SD1555 and SD1566 strains of *K. marxianus* in a BioLector fermentation.

Beta-chlorolactate resistant strains isolated as described above were compared to parent strain SD1555 for D-LAC production by fermenting in flower plates in a BioLector minifermentor (m2p-Labs, Hauppauge, N.Y., USA). Inocula for the BioLector were grown in YPD in which the dextrose concentration was lowered to 3 g/L instead of the usual 20 g/L. The fermentation medium for the BioLector was SDM2 containing 100 or 200 g/L glucose, at 1 ml per well, with a starting OD 600 nm of 0.1-0.2. The flower plates were shaken at 1200 rpm at 37° C. for 48 hours. One particular beta-chlorolactate resistant isolate, named SD1566, performed better than the parent, SD1555. The D-LAC and pyruvate titers are shown in FIG. 7. SD1566 produced a higher titer of D-LAC, and a substantially lower titer of the unwanted byproduct pyruvate, than then parent strain SD1555. A "a substantially lower titer of pyruvate when compared to a parent strain that has not been mutated" means a titer that is reproducibly at least 25% lower than that of the parent strain grown under similar conditions. SD1566 was further characterized in computer controlled 7-liter fermentors (New Brunswick Scientific, Indianapolis, Ind., USA).

Example 3

Production of D-LAC by Strain SD1566 in 7-Liter Fermenters

Figure 8:
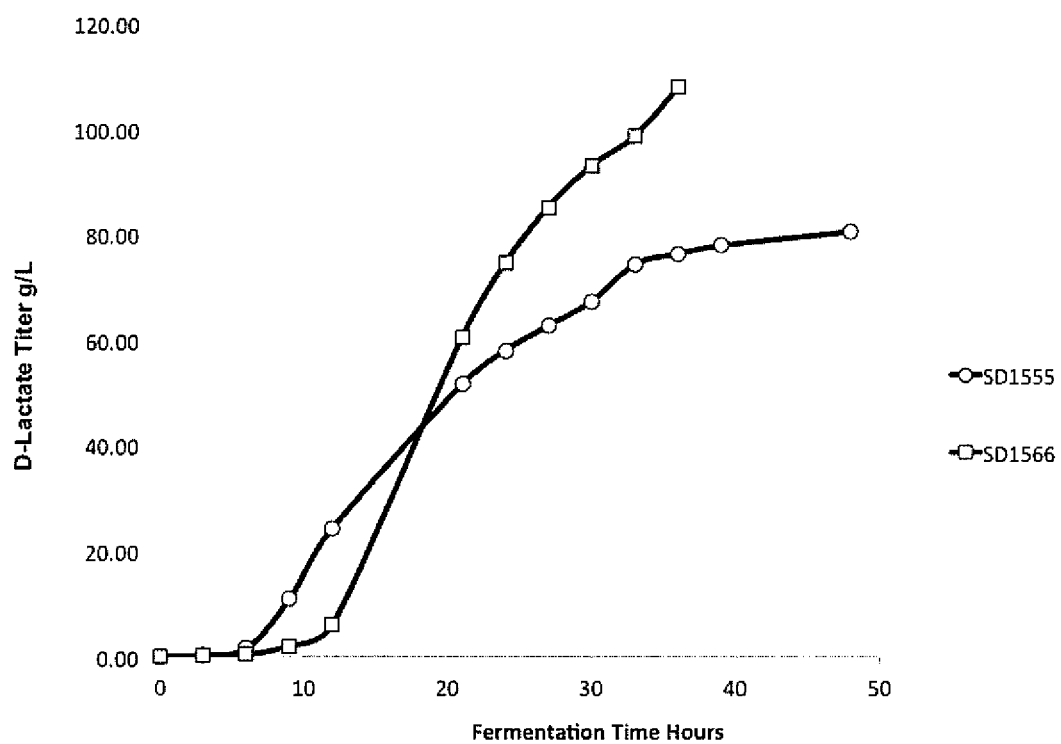
FIG. 8. Production of D-lactate and pyruvate by SD1555 and SD1566 strains of *K. marxianus* as a function of time, in computer controlled 7-liter fermentors.

Inocula of yeast strain SD1566 were grown at 37° C. in 150 ml of YPS-MES medium in 500 ml baffled shake flasks to an OD 600 nm of about 2 to 6. 150 ml was inoculated into 4 liters of AM1S medium in New Brunswick BioFlo 110 or Eppendorf BioFlo 115 fermenters. Impeller speed was 750 rpm and aeration was 260 ml/min, equal to 0.065 vvm of the starting volume. The starting pH was about 6.6. The temperature was set at 37° C. pH was controlled by automatically controlled peristaltic pumping of a slurry of 3 molar calcium hydroxide, which was kept suspended in a vigorously stirred reservoir. The starting set point was pH 6. The pH set point was automatically ramped down (i.e., decreased) to pH 3.5 in a linear fashion from time zero (inoculation time) to 30 hours. The actual pH reached 3.5 at 33 hours. At 36 hours the D-LAC titer was 110 g/L and the calculated yield was 0.81 g/g sucrose (average of duplicate fermentations). The final pyruvic acid titer was 0.55 g/L. The average specific productivity for D-LAC was 3.05 g/L-hr. For comparison, under similar conditions, the parent strain SD1555 produced 78 g/L D-LAC and 9.8 g/L pyruvate with a yield of 0.67 g/g in 39 hours. The average specific productivity for D-LAC from SD1555 was 2.0 g/L-hr. Thus, the beta-chlorolactate resistant strain SD1566 was improved for titer, yield, and average specific productivity, and its pyruvate byproduct titer was lower than that of the parent SD1555. The D-LAC titers are shown as a function of fermentation time in FIG. 8.

Using a Chirex 3126 column (Phenomenex, Torrance, Calif., USA) as recommended by the manufacturer, there was no detectable L-LAC produced by either SD1555 or SD1566. The minimum detectable titer of L-LAC by this HPLC method is 0.01 g/L, so the optical purity of the D-LAC produced by SD1566 was greater than 99.9%.

A person having ordinary skill in the art would recognize that the methods described herein could be used to add ability to produce lactic acid by genetically engineering other yeast strains, species, and genera that do not naturally produce significant titers of lactic acid, or to improve the ability to produce lactic acid by genetically engineering other yeast strains, species, and genera that already have some capacity to produce lactic acid. The insertion of the ldhA cassettes in the four target genes effectively eliminates or reduces the function of those four target genes, but alternative approaches can be used to achieve the elimination or reduction in function. Any mutation, or combination of more than one mutation, that renders the protein product of the gene to be absent, inactive, or lower in specific activity compared to that of an isogenic wild type strain, can be used to eliminate or reduce the function of any one of the four targeted genes (i.e., PDC1, GPP1, PCK1, and NDE1), or homologs or analogs of those genes. In addition, a gene encoding a D-lactate dehydrogenases other than the *E. coli* version can be used instead of the *E. coli* version, installed in one or more copies in a fashion similar to that disclosed herein. In addition, a gene encoding an L-lactate dehydrogenases can be used instead of the D-lactate dehydrogenase version, installed in one or more copies in a fashion similar to that disclosed herein.

For the fermentation process, the starting pH can vary, the final pH (when the fermentation is completed and the broth is sampled and/or harvested for downstream processing and purification of the lactic acid product) can vary, and the function, algorithm or program for lowering the pH during fermentation can vary. The pH can be ramped down with a linear function, a step function, or a non-linear, non-stepped function, for example a curved function such as an exponential or parabolic function. Regardless of the type of function, algorithm or program for pH lowering, it is preferable that the final pH is below the pKa of lactic acid in order to reduce the cost of the overall process. A starting pH of between 4.5 and 7.0 is preferable, as yeast strains typically grow faster in this range.

The material for controlling the pH in the fermentor can be any suitable alkaline material, such as the hydroxide, oxide, bicarbonate, or carbonate salt of potassium, sodium, ammonium, magnesium or calcium. The material can be fed as a solution, as a suspension or slurry, or as a solid using an auger.

The foregoing descriptions and examples have been presented for purposes of explanation. In addition to the descriptions and examples provided, numerous combinations, modifications, and variations of the features, structures, components, or characteristics of the non-limiting embodiments are possible in light of the above teachings.

Table 1 provides a summary of the best published lactic acid fermentation runs at a pH below the pKa of 3.86 in Saccharomyces cerevisiae (S. c.), Kluveromyces lactis (K m.) and Issatchenkia orientalis (I. o). Various genes used in this investigation are listed in Table 2. Table 3 lists the DNA sequence information submitted with this patent application. The compositions of the growth media used are given in Table 4.

REFERENCES

U.S. Pat. No. 6,429,006
U.S. Pat. No. 6,485,947
U.S. Pat. No. 7,049,108
U.S. Pat. No. 7,141,410
U.S. Pat. No. 7,326,550
U.S. Pat. No. 8,097,448
U.S. Pat. No. 8,137,953
U.S. Pat. No. 9,353,388
US Patent Application No. 2007/0031950A1
US Patent Application No. 2007/0092956A1
US Patent Application No. 2015/0152449A1
US Patent Application No. 2015/0240270A1
International Patent Application Publication No. WO2013/186540A1
International Patent Application Publication No. WO2015/194900A1
Abdel-Banat, B. M., S. Nonklang, H. Hoshida and R. Akada (2010) Random and targeted gene integrations through the control of non-homologous end joining in the yeast Kluyveromyces marxianus. Yeast 21(1): 29-39.
Altschul, S. F., W. Gish, W. Miller, E. W. Myers and D. J. Lipman (1990) Basic local alignment search tool. J. Mol. Biol. 215(3): 403-410.
Altschul, S. F., T. L. Madded, A. A. Schaffer, J. Zhang, Z. Zhang, W. Miller and D. J. Lipman (1997) Gapped BLAST and PSI-BLAST: a new generation of protein database search programs. Nucleic Acids Res. 25(17): 3389-3402.
Bae, J. H., H. J. Kim. M. J. Kim, B. H. Sung, J. H. Jeon, H. S. Kim. Y. S. Jin, D. H. Kweon and J. H. Sohn (2018) Direct fermentation of Jerusalem artichoke tuber poweder for production of l-lactic acid and d-lactic acid by meta-bolicallu engineered Kluyveromyces marxianus. J>Biotechnol. 266: 27-33.
Back, S. H., E. Y. Kwon, S. J. Bae, B. R. Cho. S-Y. Kim and J. S. Hahn (2017) Improvement of d-lactic acid production in Saccharomyces cerevisiae under acidic conditions by evolutionary and rational metabolic engineering. Biotechnol. J. 12(10).
Baek, S. H., E. Y. Kwon, Y. H. Kim and J. S. Hahn (2016) Metabolic engineering and adaptive evolution for efficient production of D-lactic acid in Saccharomyces cerevisiae. Appl. Nicorbiol. Biotechnol. 100(6): 2737-2748.
Dequin, S. and P. Bane (1994) Mixed lactic acid-alcoholic fermentation by Saccharomyces cerevisiae expressing the Lactobacillus casei L(+)-LDH. Biotechnology (N.Y.) 12(2): 173-177.
Porro, D. L., Brambilla, B. M. Ranzi, E. Martegani and L. Alberghina (1995) Develoment of metabolilcally engineered Saccharomyces cerevisiae cells for the production of lactic acid. Biotechnol. Prog. 11(3): 294-298.
Sauer, M., D. Porro, D. Mattanovich and P. Branduardi (2010) 16 years research on lactic acid production with yeast—ready for the market? Biotechnol. Genetic Engineer. News 27(1): 229-256.
Tsuji, H. (2005) Poly(lactide) stereocomplexes: formation, structure, properties, degradation and applications. Macromol. Biosci. 5(7): 569-597.
Van Dijken, J. P., E. van den Bosch, J. J. Hermans, L. R. de Miranda and W. A. Scheffers (1986) Alcoholic fermentation by non-fermentative yeasts. Yeast 292): 123-127.
Van Maris, A. J., W. N. Konings, J. P. van Dijken and J. T. Pronk (2004) Microbial export of lactic and 3-hydroxypropanoic acid: implications for industrial fermentation processes. Metabol. Eng. 6(4): 245-255.
Zhou, S., T. B. Causey, A. Hasona, K. T. Shanmugam and L. O. Ingram (2003) Production of optically pure D-lactic acid in mineral salts medium by metabolically engineered Escherichia coli W3110. Appl. Environ. Microbial. 69(1): 399-407.

TABLE 1

Summary of parameters of the best published L-LAC and D-LAC fermentation runs at a final pH below the pKa of 3.86 with Saccharomyces cerevisiae (S.c.); K.l., Kluveromyces lactis (K.l.); K. marxianus (K.m.; and Issatchenkia orientalis (i.o.).

| Isomer | Yeast | Titer g/L | Yield g/g | Time hours | pH | Specific Productivity g/L-hour | Reference |
|---|---|---|---|---|---|---|---|
| L | S.c. | 58 | | | 3.6 | | (Sauer, Porro et al. 2010) |
| L | S.c. | 62 | | 76 | | 0.81 | (Sauer, Porro et al. 2010) |
| L | S.c. | 70 | | 72 | | 0.97 | (Sauer, Porro et al. 2010) |
| L | K.l. | 35 | 0.44 | 97 | 3.0 | 0.36 | (Porro 2006) |
| L | I.o. | 70 | 0.75 | 69 | 3.0 | 1.5 | (Suominen 2009) |
| D | S.c. | 37 | 0.74 | 68 | 2.7 | 0.54 | (Winkler 2007) |
| D | K.m. | <62 | 0.69 | >107 | 3.0 | 0.58 | (Miller 2012) |
| D | K.m. | 49 | | 48 | 3.8 | 1.02 | (Yocum 2014) |
| D | S.c. | 82.6 | 0.83 | 55 | 3.5 | 1.50 | (Back et al. 2017) |
| D | K.m. | 110 | 0.81 | 36 | 3.5 | 3.02 | The invention |

TABLE 2

Gene names and descriptions.

| Gene name used herein | Protein or function encoded | Other names encountered in literature (not comprehensive) |
|---|---|---|
| ldhA | D-lactate dehydrigenase | ldhD, D-ldh |
| ldhL | L-lactate dehydrogenase | L-ldh |
| PDC1 | Pyruvate decarboxylase | PDC, pdc |
| GPP1 | Glycerol-3-phosphate phosphatase | |
| PCK1 | Phosphoenolpyruvate carboxylcinase | PCK, pck |

TABLE 2-continued

Gene names and descriptions.

| Gene name used herein | Protein or function encoded | Other names encountered in literature (not comprehensive) |
|---|---|---|
| NDE1 | NADH dehydrogenase 1 | |
| TEF1 | Translation elongation factor 1 | eft, eftu, eftU |
| CYC1 | Cytochrome C | |

TABLE 3

Sequence information

| | |
|---|---|
| SEQ ID 1 | Sequence of the plasmid pMS52 |
| SEQ ID 2 | Sequence of the plasmid pSD100 ldhA |
| SEQ ID 3 | Sequence of the plasmid pSD95 ldhA |
| SEQ ID 4 | Sequence of the plasmid pSD100 PCK1 |
| SEQ ID 5 | Sequence of the plasmid pSD104 NDE1 |
| SEQ ID 5 | Wt KmURA3 gene and 1033 bp upstream flanking sequence and 1046 bp downstream flanking sequence of the URA3 gene of strain SD98 |

TABLE 4

Composition of growth media. All amounts listed are per liter.
For Petri plates, 20 g/L agar was added.

| Ingredient | CM minus uracil | SDM2 | AM1S | YPD | YPS-MES |
|---|---|---|---|---|---|
| Glucose | | (20-200 g) | | 20 g | |
| sucrose | | (20-200 g) | 200 | | 20 g |
| Teknova CM-ura mix | One 1 L pack | | | | |
| Potassium phosphate monobasic | | | 0.51 g | | |
| Ammonium phosphate monobasic | | 13.8 g | 0.87 g | | |
| Ammonium phosphate dibasic | | 3.96 g | 2.63 | | |
| Magnesium sulfate. 7H$_2$O | | 0.493 g | 0.37 g | | |
| Yeast extract | | | | 10 g | 10 g |
| Peptone | | | | 20 g | 20 g |
| Thiamine HCl | | 200 mcg | 0.1 mg | | |
| Niacin | | 3 mg | 4 mg | | |
| Biotin | | 10 mcg | 0.01 mg | | |
| Calcium pantothenate | | 400 mcg | 0.4 mg | | |
| 1000 X trace elements* | | 1 ml | 1 ml | | |
| pH (with ammonium hydroxide or phosphoric acid) | | 6.2 | 6.6 | | 6.0 |
| MES (2-(N-morpholino) ethanesulfonic acid) | | | | | 19.5 |
| Betaine | | | 0.117 g | | |
| Sodium Chloride | | 0.234 g | | | |
| Potassium Chloride | | 0.521 g | | | |

*1000 X Trace elements, per liter: 1.6 g FeCl$_3$•6H$_2$O, 0.1 g CuCl$_2$•2H$_2$O, 0.2 g ZnCl$_2$, 0.05 g H$_3$BO$_3$, 0.55 g MnCl$_2$•4H$_2$O, 10 mL 85% phosphoric acid

What is claimed is:

1. A genetically engineered yeast strain of genus *Kluyveromyces* to produce lactic acid comprising a chromosomally integrated gene that encodes an exogenous lactate dehydrogenase, wherein said yeast strain produces lactic acid in a fermentation production medium with an average specific productivity of at least 1.875 g/L-hr, and wherein said fermentation production medium has a final pH that is lower than 3.86, wherein said gene that encodes an exogenous lactate dehydrogenase is integrated at least at one chromosomal locus selected from a group consisting of a pyruvate decarboxylase gene, a phosphoenolpyruvate carboxykinase gene, a glycerol-3-phosphate phosphatase gene, and a NADH dehydrogenase 1 gene.

2. A yeast strain of claim 1, wherein said yeast strain produces lactic acid in a fermentation production medium with an average specific productivity of at least 3.00 g/L-hr.

3. A yeast strain of claim 1, wherein said yeast strain produces lactic acid in a fermentation production medium with an average specific productivity of at least 3.00 g/L-hr and a final pyruvic acid titer of less than 1 g/L.

4. The yeast strain of claim 1, wherein said yeast strain is resistant to a lactic acid analogue.

5. The yeast strain of claim 4, wherein said lactic acid analogue is selected from a group consisting of 3-chlorolactate (beta-chlorolactate), 3,3-dichlorolactic acid, 3,3,3-trichorolactic acid, 3-fluorolactic acid, 3,3-difluorolactic acid, 3,3,3-trifluorolactic acid, 3-bromolactic acid, 3,3-dibromolactic acid, 3,3,3-tribromolactic acid, all possible 2-halo-substituted derivatives of lactic acid, all chiral forms of any of the above lactic acid analogs and any salt of any of the lactic acid analogs.

6. The yeast strain of claim 1, further comprising a mutation that eliminates or reduces the function of one or more genes selected from the group consisting of phosphoenolpyruvate carboxykinase gene (PCK1), NADH dehydrogenase 1 gene (NDE1), pyruvate decarboxylase gene (PDC1), and glycerol-3-phosphate phosphatase gene (GPP1).

7. The yeast strain of claim 1, wherein said lactic acid is optically pure D-lactic acid.

8. The yeast strain of claim 1, wherein said lactic acid is optically pure L-lactic acid.

9. The yeast strain of claim 1, wherein said lactic acid is a mixture of D-lactic acid and L-lactic acid.

10. A process for producing lactic acid comprising:
   (a) providing the yeast strain and the fermentation production medium of claim 1; and
   (b) culturing said yeast strain in said fermentation production medium; and
   (c) recovering lactic acid from the fermentation production medium.

\* \* \* \* \*